(12) United States Patent
Mendez

(10) Patent No.: US 7,932,048 B2
(45) Date of Patent: Apr. 26, 2011

(54) METHOD FOR THE IN VITRO DIAGNOSIS OF ALZHEIMER'S DISEASE USING A MONOCLONAL ANTIBODY

(75) Inventor: Enrique Mendez, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 369 days.

(21) Appl. No.: 11/886,022

(22) PCT Filed: Mar. 9, 2006

(86) PCT No.: PCT/ES2006/070027
§ 371 (c)(1),
(2), (4) Date: May 12, 2008

(87) PCT Pub. No.: WO2006/095041
PCT Pub. Date: Sep. 14, 2006

(65) Prior Publication Data
US 2009/0023159 A1    Jan. 22, 2009

(30) Foreign Application Priority Data

Mar. 9, 2005   (ES) .................................. 200500550

(51) Int. Cl.
*G01N 33/53*   (2006.01)
*G01N 33/563*  (2006.01)
*C12P 21/08*   (2006.01)
(52) U.S. Cl. ......... 435/7.9; 435/7.1; 435/70.2; 436/512; 530/388.1
(58) Field of Classification Search ........................ None
See application file for complete search history.

(56) References Cited

U.S. PATENT DOCUMENTS

| 4,666,829 A | 5/1987 | Glenner et al. |
| 5,688,651 A | 11/1997 | Solomon |
| 5,958,883 A | 9/1999 | Snow |

FOREIGN PATENT DOCUMENTS

| EP | 0 683 234 | 11/1995 |
| WO | 90/12871 | 11/1990 |
| WO | 97/21728 | 6/1997 |

OTHER PUBLICATIONS

Rabano Oct. 2005 (Current Alzheimer Research 2(4):409-417).*
Asami-Odaka 1995 (Biochemistry 34:10272-10278).*
Oshima 2001 (American Journal of Pathology 158:2209-2218).*
Enya 1999 (American Journal of Pathology 154:271-279).*
Vector Laboratories 2005 catalog (published 2005, pp. 3-15 and 32-36).*

* cited by examiner

*Primary Examiner* — Daniel E Kolker
(74) *Attorney, Agent, or Firm* — Ladas & Parry LLP

(57) ABSTRACT

The invention relates to a method for the in vitro diagnosis of Alzheimer's disease using a monoclonal antibody. Said antibody can bind at least to amino acids 12-16 of the β-amyloid peptide, specifically detecting the neuritic plaques which are characteristic of Alzheimer's disease, without detecting diffuse plaques which are not defining characteristics of the disease. Within the neuritic plaques, the monoclonal antibody can detect a different sub-group in the composition of the different deposited isoforms of the β-amyloid peptide, which is associated with the disease progression stage. In addition, the antibody can bind to isoforms of the β-amyloid peptide in biological fluids such as urine. As a result, the inventive monoclonal antibody, the cell lines that produce said antibody and compositions containing same can be used in the in vitro diagnosis of Alzheimer's disease and in determining the disease progression stage.

41 Claims, 7 Drawing Sheets

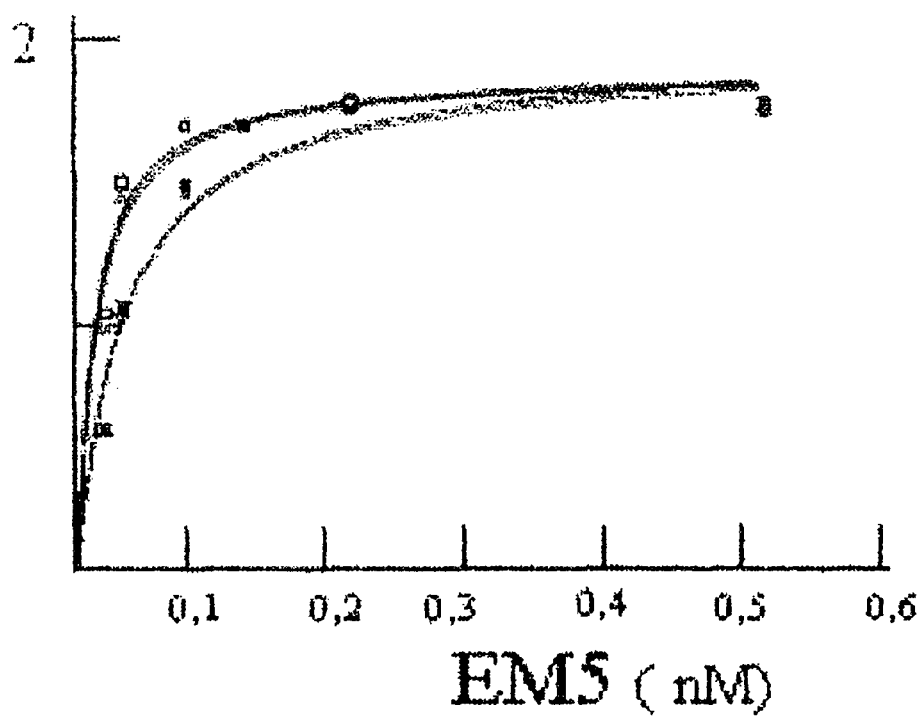
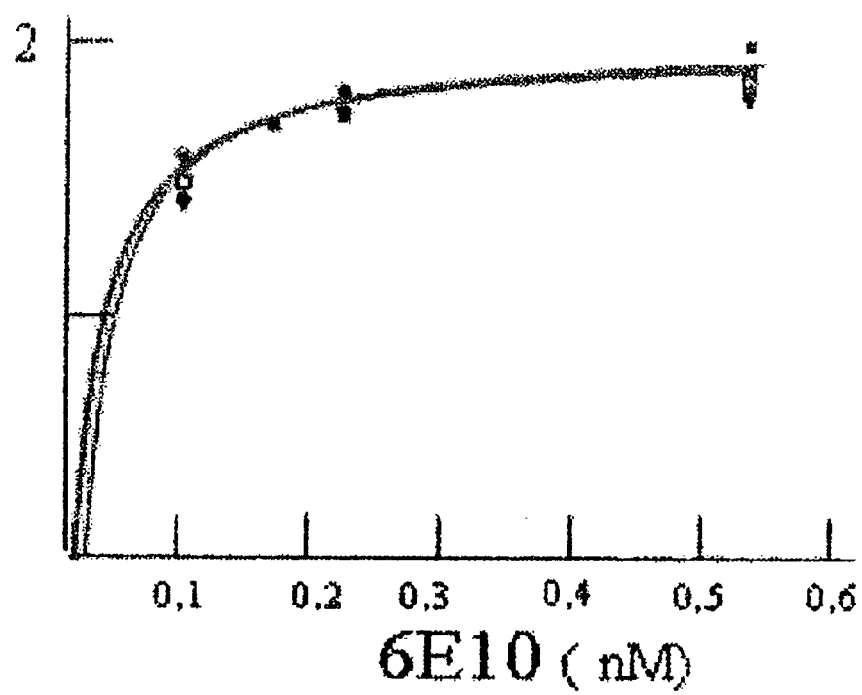
Figure 1

SEQUENCE LISTING

```
<160> NUMBER OF SEQ ID NOS: 4

<210> SEQ ID NO 1
<211> LENGTH: 10
<212> TYPE: PRT
<213> ORGANISM: artificial
<220> FEATURE:
<223> OTHER INFORMATION: portion of amyloid peptide
<300> PUBLICATION INFORMATION:
<310> PATENT DOCUMENT NUMBER: US4666829
<311> PATENT FILING DATE: 1985-05-15
<312> PUBLICATION DATE: 1987-05-19

<400> SEQUENCE: 1

Asp Ala Glu Phe Arg His Asp Ser Gly Tyr
1               5                   10

<210> SEQ ID NO 2
<211> LENGTH: 17
<212> TYPE: PRT
<213> ORGANISM: artificial
<220> FEATURE:
<223> OTHER INFORMATION: b-amyloid peptide
<220> FEATURE:
<221> NAME/KEY: MISC_FEATURE
<222> LOCATION: (1)..(17)
<223> OTHER INFORMATION: 6E10, SV17-6E10
<300> PUBLICATION INFORMATION:
<310> PATENT DOCUMENT NUMBER: WO 90/12871
<311> PATENT FILING DATE: 1990-04-13
<312> PUBLICATION DATE: 1990-11-01

<400> SEQUENCE: 2

Asp Ala Glu Phe Arg His Asp Ser Gly Tyr Gln Val His His Gln Lys
1               5                   10                  15

Leu

<210> SEQ ID NO 3
<211> LENGTH: 5
<212> TYPE: PRT
<213> ORGANISM: human

<400> SEQUENCE: 3

Val His His Gln Lys
1               5
```

```
-continued

<210> SEQ ID NO 4
<211> LENGTH: 8
<212> TYPE: PRT
<213> ORGANISM: artificial
<220> FEATURE:
<223> OTHER INFORMATION: Coupling tail for the design of the amino
      Terminal end of Ab37-42y Ab37-49

<400> SEQUENCE: 4

Cys Ser Gly Gly Ser Gly Gly Gly
1               5
```

METHOD FOR THE IN VITRO DIAGNOSIS OF ALZHEIMER'S DISEASE USING A MONOCLONAL ANTIBODY

FIELD OF THE INVENTION

The present invention relates to the diagnosis of neurological disorders, especially to the diagnosis of Alzheimer's disease by means of an antibody that is able to interact with specific peptides associated with said disease.

BACKGROUND OF THE INVENTION

Alzheimer's disease (AD) is a neurological disorder that causes the death of neurons in the brain. Generally it progresses slowly, commencing after age 50 years, and its first symptoms may be attributed to old age or to ordinary forgetfulness. As the disease progresses, there is gradual deterioration of cognitive abilities, including the ability to take decisions and carry out everyday tasks, and there may be changes in personality, as well as behavioral problems. In its advanced stages, AD leads to dementia and finally to death. At present the disease is incurable and constitutes a major cause of mortality.

At the present time, Alzheimer's disease is normally diagnosed from the clinical picture, since a definitive diagnosis can only be based on histological examination of brain samples (autopsy or biopsy), revealing the presence of its characteristic features in the brain tissue. In view of the risks associated with brain biopsy in live patients, this procedure is very rarely used, and accordingly it is estimated that the error rate in in-vivo diagnosis of this disease is around 20-30%.

The brains of individuals with Alzheimer's disease show two principal pathological markers: neurofibrillary degeneration (which is identified by the presence of neurofibrillary tangles, dystrophic neurites and neuropil threads) and deposits of amyloid substance (i.e. deposits of so-called β-amyloid peptide, generally abbreviated to Aβ), both in the form of plaques (diffuse plaques and neuritic plaques, these last-mentioned forms being characteristic of the disease, and being designated as such since they appear between and within the neurons), and in the form of vascular deposits (which occur in the walls of the cerebral blood vessels). Both neurofibrillary degeneration and amyloid deposition constitute degenerative processes that are also associated with normal ageing of the brain. In elderly subjects who are not suffering from dementia, the Aβ peptide is mainly deposited in the form of diffuse plaques. This type of deposition is especially pronounced in some subjects with normal cognitive abilities, and for some authors constitutes a process of "pathologic ageing", which is regarded as being half-way between normal ageing of the brain and AD [1]. Particularly intensive, premature development of diffuse plaques years before neuritic plaques appear also takes place in Down's syndrome (DS), due to trisomy of chromosome 21 which leads to overexpression of the amyloid precursor protein (β-APP). Although a small number of neuritic plaques may be observed in the brains of subjects with normal cognitive abilities, brains affected by AD as well as those affected by DS in the elderly are characterized by the development of a large quantity of mature neuritic plaques [2, 3]. In contrast to the diffuse plaques, which contain a nonfibrilary form of Aβ (designated "preamyloid") [4], both the vascular amyloid deposits and the neuritic plaques contain Aβ peptide in fibrillary form and react with stains of amyloid substance such as Congo Red and Thioflavine T.

The cognitive decline in AD is correlated linearly with the progression of the neurofibrillary changes and cortical synapse loss [5]. Local synapse loss associated with diffuse plaques has not been observed [6]. In contrast, neuritic plaques are associated with synaptic density loss, neurofibrillary change and activation of the microglia [7]. Both the pure neurofibrillary change and the deposition of Aβ follow well established sequential patterns of progression in AD [8,9]. However, although the degree of cognitive decline has better correlation with a succession of stages based on neurofibrillary change [5], the definitive neuropathologic diagnosis of AD is nevertheless based on histological demonstration of a significantly higher density of neuritic plaques in the associative neocortical regions, relative to that expected according to the patient's age group, within a clinical picture of dementia (consensus criteria of CERAD: *Consortium to Establish a Registry for Alzheimer's Disease*) [10]. The formation of neuritic plaques constitutes the central pathogenic process in AD, and the molecular composition of these β-amyloid deposits and the differences from the diffuse plaques in relation to said composition is accordingly one of the main fields of interest in current research into AD.

Knowledge about the molecular composition of the β-amyloid deposits in the brain tissue of patients with Alzheimer's disease has changed radically during recent years. Various studies employing biochemical or immunohistochemical methods with the aim of identifying different forms of the Aβ peptide have supplied a fairly consistent picture that permits a molecular interpretation of the classical morphological findings. It was these studies that provided the basis for the unified pathogenic theory of the disease, called the amyloid hypothesis [1,1], although the original hypothesis has been reformulated recently in order to include the emergent role of the soluble Aβ oligomers as the principal pathogenic agents [12]. The assumption of a central and primary pathogenic role of the Aβ peptides in AD is now leading to new therapeutic strategies directed at the prevention or removal of these deposits.

The topographic distribution and temporal sequence of the deposition of Aβ peptides known in brains affected by AD have been elucidated by means of antibodies directed at the carboxyl end, the amino end or to internal segments of the Aβ molecule, together with the isolation and purification of isoforms of Aβ by biochemical methods. The tissue distribution of peptides characterized by the features of their carboxyl ends shows a fairly regular, well-defined pattern. Whereas $A\beta_{X-40}$ is the predominant form in the vascular deposits and is the main form encountered in the CSF (cerebrospinal fluid), $A\beta_{X-42}$ is the main form detected in the brain tissue deposits (diffuse plaques and neuritic plaques) [13]. In AD, Down's syndrome (DS) [13, 14] and normal ageing [1], $A\beta_{X-42}$ is the only component of the diffuse plaques and the principal component of the neuritic plaques. The latter may also contain $A\beta_{X-40}$, predominantly in the region of their central nucleus. It has also been established that $A\beta_{X-42}$ is the form that is deposited in the initial stages.

Although it was believed initially that $A\beta_{X-40}$ and $A\beta_{X-42}$ began almost entirely with the amino acid Asp1, it has been well established immunohistochemically and biochemically that a wide variety of heterogeneous isoforms of the Aβ peptide, modified and truncated at the amino end, participate in the composition of both the diffuse and the neuritic plaques [15]. These isoforms also tend to show a regular pattern of distribution between the diffuse and neuritic plaques, so that a complete picture of the topographical distribution of the various Aβ peptides has finally begun to emerge. There are, nevertheless, some discrepancies between the studies, particularly with respect to the characteristics of the amino end of the peptides that make up the diffuse plaques, and the relative amount of amyloid deposit each of them represents.

These discrepancies involve the p3 peptide ($A\beta_{17-42}$) in particular. Whereas some studies suggest that $A\beta_{17-42}$ may be the principal component of the diffuse plaques [16], others have found a relatively larger amount of longer forms (beginning at Asp1, or truncated at the amino end or other modified isoforms) at this level [15]. Since $A\beta_{17-42}$ is produced by excision of β-APP by α-secretase (the so-called nonamyloidogenic pathway) and displays physicochemical properties quite different from the longer isoforms of Aβ (the later being generated by excision of β-APP by γ-secrete), its selective presence in diffuse plaques may be of crucial pathogenic significance in the development of the plaques.

Gowing et al. [17] were the first to isolate the $A\beta_{17-42}$ peptide as the predominant form recovered from brains affected by AD rich in diffuse plaques. This deposit was not found in vascular amyloid deposits or in neuritic plaques. The commercial monoclonal antibody 6E10, which recognizes $A\beta_{1-17}$, did not produce immunostaining of diffuse plaques, neither neocortical nor cerebellar, in a series of brains affected by AD and DS [18]. However, the corpus striatum, where the diffuse plaques are particularly abundant in the absence of neuritic plaques, showed some plaques that are positive for the 6E10 antibody. Using HPLC and immunohistochemical determinations, Lalowski et al. [19] demonstrated that $A\beta_{17-42}$ represents 70% of the total amyloid content in diffuse plaques of the cerebellum, whereas $A\beta_{1-42}$ represents 12% and other truncated forms of $A\beta_{X-42}$ represent 5% or less. In brains of elderly persons affected by DS, Saido et al. [20] found greater staining of diffuse plaques with a specific anti-Aβ N3 (pyroGlu) antibody than with an anti-Aβ N(1) antibody. Iwatsubo et al. [15] studied diffuse plaques in a series of brains from elderly persons, affected by AD and affected by DS with a panel of antibodies directed at recognizing forms of Aβ truncated and modified at the amino end. This study is unique in that the brain tissue employed for the immunohistochemical investigation was fixed either in 70% ethanol, or in 4% formaldehyde, so as to be able to test the effect of routine fixing with formaldehyde on the appearance of artefacts. In all the tissue samples fixed in 70% ethanol, the diffuse plaques were stained intensely by the presence of Aβ N1 (L-Asp), Aβ N1 (L-isoAsp), Aβ N1 (D-Asp), Aβ N3 (pyroGlu), and $A\beta_{X-42}$. Weak immunostaining was obtained with Aβ N11 (pyroGlu) and Aβ N17. However, in the material fixed in formaldehyde some diffuse plaques were stained with Aβ N1 (L-Asp), and no staining was obtained with Aβ N1 (L-isoAsp) or Aβ N1 (D-Asp), whereas the pattern of staining for the carboxyl end was unchanged. Although the authors demonstrated that modification of the amino end can alter the results of immunostaining in tissues fixed in formaldehyde, they obtained weak reactivity for Aβ N17 even in material fixed in ethanol. Using a monoclonal antibody specific to p3 ($A\beta_{17-42}$) [16], they found that deposition of this peptide was largely limited to diffuse plaques, dystrophic neurites and the coronas of neuritic plaques in the regions of the amygdalas, hippocampus and parahippocampus. The authors suggested a specific role of p3 in the initial deposition of amyloid substance and in the origin of the neuritic plaques. Tekirian et al. [21] demonstrated, in a series of brains affected by AD and controls, the presence of Aβ N3 (peptide)>Aβ N1 (D)>Aβ N17 (L)>Aβ N1 (rD) in the diffuse plaques.

With regard to variability at the carboxyl end, in a study using antibodies directed against $A\beta_{X-40}$, $A\beta_{X-42}$ or $A\beta_{X-43}$, Parvathy et al. [22] found a subgroup of neuritic plaques that only react to the Aβ C40 antibody and a larger subgroup of plaques that react both to a Aβ C40 and to Aβ C42.

Earlier studies have thus established that the diffuse plaques show a profile of Aβ that is highly specific at the carboxyl end and a profile that is fairly specific at the amino end, the latter being subject to some heterogeneity between patients and between different regions of the brain. The presence of $A\beta_{17-42}$ appears to be limited largely to the diffuse plaques, although there is considerable variation between the studies with respect to the relative contents of this shorter peptide in them. In the studies conducted by Kida et al. [18], no staining was obtained for Aβ peptides that included the sequence 12-16 in diffuse plaques of cortical and subcortical regions.

Considered overall, the results of the State of the Art (SA) suggest that, as proposed by Larner [23], the forms of the Aβ peptide that are specific according to the amino end can play an essential role in the development of the diffuse plaques so that they are converted to neuritic plaques. Therefore antibodies capable of specifically detecting forms with the amino end truncated and, accordingly, clearly differentiating between diffuse plaques and neuritic plaques are extremely useful as tools in the diagnosis of Alzheimer's disease. Among them, those that are able to differentiate subgroups of neuritic plaques according to the proportion of the different forms of amyloid peptide that differ in the amino acid terminating the carboxyl end would be especially useful, especially if they could be used for defining subsets of plaques that constitute a specific disease marker. The monoclonal antibody of the invention, directed against the sequence constituted of amino acids 12-16 of β-amyloid peptide and with greater affinity for the Aβ42 form than the Aβ40 form, fulfils both characteristics.

Another aspect in which the antibodies that are able to detect forms of β-amyloid peptide would be particularly useful would be in the diagnosis of Alzheimer's disease by analysis of the concentration of different forms of this peptide in biological fluids, an aspect that is being investigated both to facilitate diagnosis based on biochemical parameters, and even with a view to identifying preclinical cases or those at particular risk of developing the disease and for monitoring patients enrolled in clinical studies. For this purpose, many studies focus on the cerebrospinal fluid (CSF), with the aim of detecting whether there are variations in the concentrations of soluble forms of β-amyloid peptide present in this fluid that make it possible to differentiate between patients and healthy controls. However, it is rather unlikely that analysis of the CSF, which involves the use of an invasive technique, lumbar puncture, could be applied for the diagnosis and routine monitoring of patients with Alzheimer's disease in clinical practice. Therefore other lines of research have focused on investigation of variations in the concentration in blood and urine of biological markers (which include soluble forms of β-amyloid peptide) which might be correlated with the appearance and development of the disease, although few studies have been published to date. According to these, the plasma levels of $A\beta_{X-42}$ and $A\beta_{X-40}$ appear to be increased if there is Down's syndrome and they also increase in normal individuals with age. The plasma levels of $A\beta_{X-42}$, but not of $A\beta_{X-40}$, are raised in patients with Alzheimer's disease, and decrease as the disease develops [28, 29], although measurement of the concentration of these species in plasma cannot currently be applied in diagnosis. The presence of soluble forms of β-amyloid peptide has also been detected in urine [30], although a comparative study between patients and controls has not yet been carried out. Although the order of magnitude of the concentrations of β-amyloid peptide that are being detected in plasma and urine are making it difficult to define the profiles corresponding to healthy individuals and to patients in different stages of the disease and the possible association of the soluble forms of β-amyloid peptide with other proteins present in said biological fluids is another difficulty to be overcome, this is an approach being actively pursued, so that the monoclonal antibodies that can interact with forms of β-amyloid peptide present in biological fluids to make it possible to detect them can represent a very useful tool in the diagnosis of Alzheimer's disease. The antibody of the invention, which is able to interact with soluble forms of β-amyloid peptide and detect their presence in biological fluids such as urine, is one of the antibodies that may be useful for implementing these diagnostic techniques. Moreover, the fact that it is directed specifically against the region close to the amino end of β-amyloid peptide is a characteristic of interest in the differentiation of the forms of β-amyloid peptide that conserve the amino end from those forms in which said end is truncated.

Other monoclonal antibodies directed specifically against the region close to the amino end of β-amyloid peptide, as well as their use in diagnostic methods connected with AD, have been described. For example, U.S. Pat. No. 4,666,829 describes the production of a monoclonal antibody generated against a portion of the amyloid peptide closest to the amino end. Concretely, a synthetic peptide was prepared comprising the first ten residues of said peptide (Asp-Ala-Glu-Phe-Arg-His-Asp-Ser-Gly-Tyr), represented by SEQ ID NO: 1. The epitope recognized by this antibody % kill be included in these amino acids 1 to 10, whereas the antibody claimed in the present invention recognizes at least the epitope that comprises the amino acids from 12 to 16. As well as differing in the specific sequence that recognizes this monoclonal antibody with respect to that of the present invention, the design of the proposed diagnostic technique is also different, since what is determined is exclusively the binding of the antibodies used to what is considered in this patent to be the peptide that is characteristic of Alzheimer's disease, that constituted by amino acids 1 to 28 of the amyloid peptide, without considering binding to other forms of the peptide of different lengths and/or with variations in the amino and carboxyl ends. Moreover, no experimental proof is given that demonstrates its capacity for detecting forms of the amyloid peptide present in biological fluids.

Furthermore, patent application PCT WO 90/12871 describes the preparation of the monoclonal antibody designated SV17-6E10. This antibody is generated by immunization with the peptide sequence Asp-Ala-Glu-Phe-Arg-His-Asp-Ser-Gly-Tyr-Gln-Val-His-His-Gln-Lys-Leu, represented by SEQ ID NO:2, which might be considered equivalent to that of amino acids 1 to 17 of the amyloid peptide. Another monoclonal antibody directed against the region that includes amino acids 1 to 17 is the aforementioned commercial monoclonal antibody 6E10 which, as pointed out in the description of the data sheet corresponding to the product, http://www.alexis_corp.com/monoclonal:antibodies-SIG-9320/opfa.1.1.SIG-9320.386.4.1.html, specifically, within amino acids 1 to 17 of β-amyloid peptide, recognizes the epitope comprised between amino acids 3 to 8. This epitope corresponds to a different region, closer to the amino end than that of the EM5 monoclonal antibody of the invention. Although it is capable of producing differential staining of neuritic plaques and vascular deposits, without staining the diffuse plaques, this antibody does not appear to display differences in affinity between peptides Aβ42 and Aβ40.

Accordingly, the monoclonal antibody of the invention, which has been designated EM5, constitutes a novel tool, because it recognizes at least one epitope that is not recognized by any of the antibodies described in the known state of the art, in the sequence of β-amyloid peptide. The antibody of the invention is, accordingly, useful for application in the diagnosis of Alzheimer's disease. It detects neuritic plaques specifically without detecting diffuse plaques, which are not specifically associated with the disease. Among the neuritic plaques, the monoclonal antibody of the invention makes it possible to detect a subgroup of neuritic plaques differing in their molecular composition relative to the deposits of β-amyloid peptide. Moreover, the monoclonal antibody of the invention is capable of binding to forms of β-amyloid peptide present in solution, permitting subsequent detection and quantification of said peptides, including if the solution is a biological fluid such as urine.

SUMMARY OF THE INVENTION

The invention relates to a monoclonal antibody that recognizes, in β-amyloid peptide, the epitope corresponding to the sequence:
Val-His-His-Gln-Lys (SEQ ID NO:3)
and is capable of binding to isoforms of β-amyloid peptide that contain said sequence, regardless of whether the peptide is in soluble form, aggregated form or denatured by SDS, although displaying greater affinity for the Aβ 42 isoform than for the Aβ 40 isoform.

The invention also relates to fragments of the aforesaid antibody that are also capable of binding to isoforms of β-amyloid peptide that contain said SEQ ID NO:3.

The invention also relates to a hybridoma cell line capable of producing the monoclonal antibody previously described and to a method of producing said antibody by obtaining a hybridoma cell line and culture of said cell line in conditions that permit the production of the monoclonal antibody.

Additionally, the invention relates to a composition comprising the antibody of the invention or at least one fragment thereof capable of binding to SEQ ID NO:3. A possible embodiment of a composition of the invention is that in which the antibody or the fragment thereof is coupled to a substance that enables it to be detected, said substance being a second antibody capable of binding to the antibody of the invention or to the fragment thereof and that is coupled to a substance that can enable it to be detected, such as an enzyme capable of catalyzing the conversion of a particular substance into another that can be detected, for example a chromogen. Another possible embodiment of a composition of the invention is that in which the antibody or a fragment thereof is coupled to some substance or particle that facilitates extraction of isoforms of β-amyloid peptide present in a solution, such as a magnetic particle that will permit separation of the solution of antigen-antibody or antigen-antibody fragment complexes formed if a magnetic field is applied, it thus being possible to concentrate the isoforms of β-amyloid peptide present in said solution and facilitate their subsequent detection, identification and/or quantification.

The invention also relates to the use of the monoclonal antibody of the invention or at least one fragment thereof capable of binding to SEQ ID NO:3 for detecting isoforms of β-amyloid peptide that contain SEQ ID NO:3. The isoforms of β-amyloid peptide to be detected can be present in a sample of brain tissue taken from an individual, in a solution such as a sample of a biological fluid or a solution derived therefrom or can even be contained in some other, non-biological type of sample, in which it is similarly desired to detect the possible presence of isoforms of β-amyloid peptide.

Finally, the invention relates to a method of in-vitro diagnosis of Alzheimer's disease based on the detection of isoforms of β-amyloid peptide by using the antibody of the invention, or of at least one fragment thereof capable of binding to SEQ ID NO:3. In a preferred embodiment of the invention, the isoforms of β-amyloid peptide are detected in a sample of brain tissue taken from an individual. In this case, the compositions of the invention in which the antibody or the fragment thereof is coupled to a substance that is able to permit their detection, said substance possibly being a second antibody capable of binding to the antibody of the invention or to a fragment thereof and is coupled to another substance that is able to permit its detection, can be particularly useful.

In another preferred embodiment of the diagnostic technique of the invention, the isoforms of β-amyloid peptide are detected in a solution, preferably a sample of a biological fluid such as cerebrospinal fluid, urine or blood, or even a solution derived from a biological fluid, such as plasma. In this second embodiment of the invention, it is preferred to use compositions of the invention in which the antibody or the fragment thereof is coupled to some substance or particle that facilitates the extraction of isoforms of β-amyloid peptide present in solution, such as a magnetic particle that will permit the separation of the antigen-antibody or antigen-antibody fragment complexes formed from the solution, if a magnetic field is applied, it thus being possible to concentrate the isoforms of β-amyloid peptide present in the solution and facilitate their subsequent detection, identification and/or quantification. Accordingly, the method of diagnosis of the invention comprises the stages of:

a) addition of a composition that comprises the antibody of the invention or at least one fragment thereof capable of binding to SEQ ID NO:3 coupled to a magnetic particle, to the sample of biological fluid or the solution derived therefrom;

b) waiting a sufficient time for antigen-antibody or antigen-antibody fragment complexes to form between at least one isoform of β-amyloid peptide and the antibody or fragment of antibody contained in the composition;

c) application of a magnetic field for extracting the antigen-antibody or antigen-antibody fragment complexes from the solution;

d) removal of the solution;

e) separation of the antibody or fragment of antibody from the molecules of β-amyloid peptide;

f) identification and quantification of the isoforms of β-amyloid peptide extracted from the sample of biological fluid or solution derived therefrom.

The solution from which the isoforms of β-amyloid peptide are extracted is preferably a sample of blood or urine, as they are simpler to obtain than in the case of samples of cerebrospinal fluid, or alternatively a plasma sample derived from a blood sample. Between blood or plasma and urine, it is especially preferred that the sample of biological fluid is a urine sample, which can be obtained without the use of invasive methods. However, it is then essential to use a very sensitive method for identifying and quantifying the isoforms of β-amyloid peptide, such as MALDI-TOF mass spectrometry.

The polyclonal antibodies EM2 and EM3, which were also developed by the present inventors, can also be used as an additional tool in the method of diagnosis of the invention.

BRIEF DESCRIPTION OF THE DRAWINGS

FIG. 1 shows the curves of binding of the antibodies EM5 (top part) and 6E10 (bottom part) to immobilized Aβ peptides. It shows the results corresponding to different concentrations (abscissa; in concentration nM) of the antibodies both to the Aβ 40 peptide (filled symbols) and to the Aβ 42 peptide (empty symbols), in both cases aggregated (Δ) or without aggregation (□). Each point represents the mean value from experiments carried out in triplicate. The optical density (O.D.) at 450 nm is shown on the ordinate.

FIG. 5 shows photographs of immunostainings of brain tissue affected by Alzheimer's disease, using EM2, EM3, EM5 and combinations of EM5 with each of the aforementioned. The structures stained are labelled as V (vessels), DP (diffuse plaques) and NP (neuritic plaques). The photographs correspond to:

(A) and (B): Consecutive serial sections of the same zone of the occipital cortex immunostained with EM5 (A) and EM 3 (B) as primary antibody, using nitroblue tetrazolium (NBT) as chromogen.

(C): Micrograph at high magnification from a double immunostaining technique using EM3 (chromogen: NBT) and EM5 (chromogen: DAB) as primary antibodies.

(D) and (E): Consecutive serial sections of the same area of the occipital cortex immunostained either with EM5 (D) or with EM2 (E).

(F): Microphotograph at high magnification from a double immunostaining technique using EM2 (chromogen: nitroblue tetrazolium, NBT) and EM5 (chromogen: diaminobenzidine, DAB).

Figure 6:
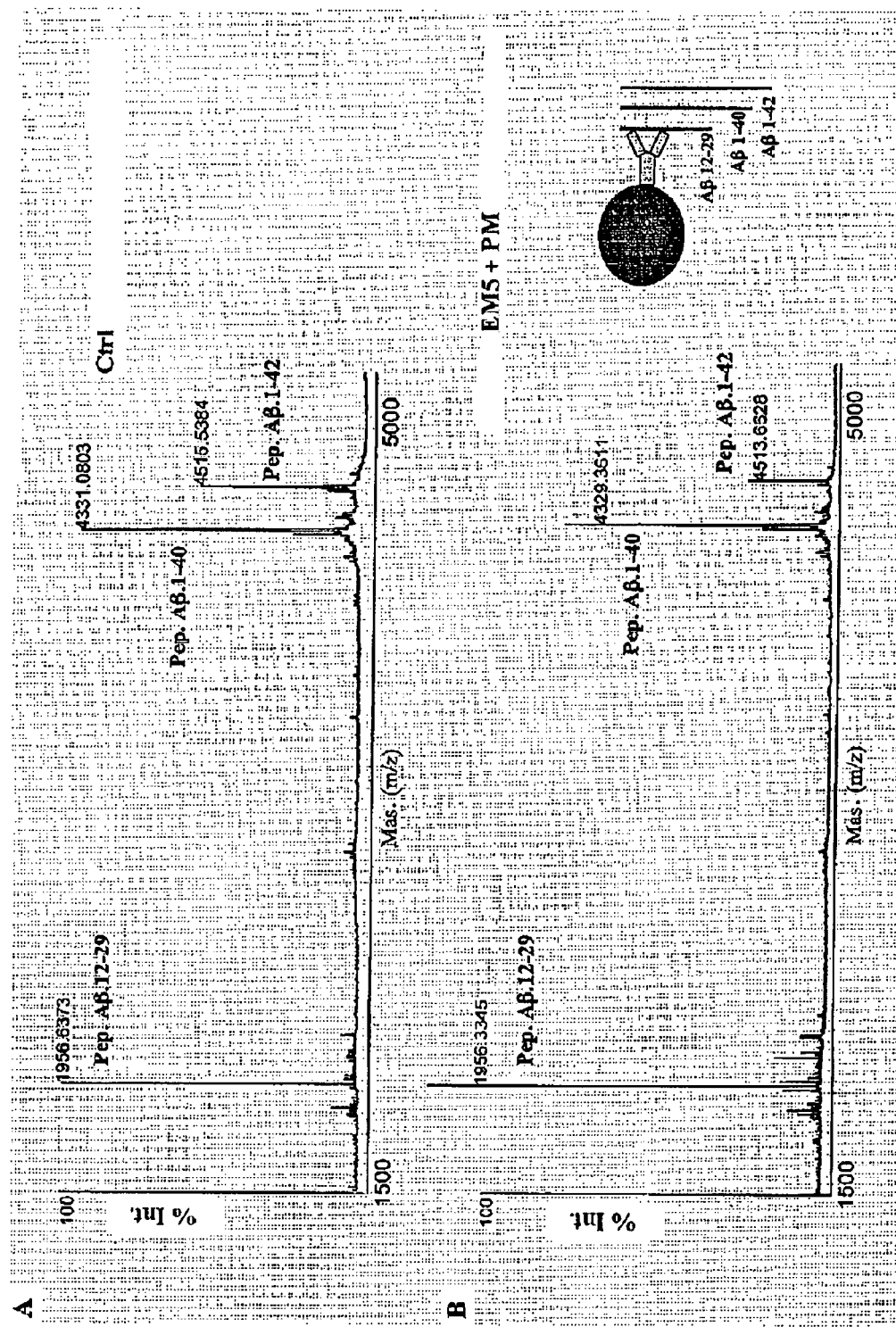

FIG. 6 shows graphs obtained in analysis by MALDI-TOF mass spectrometry of forms of β-amyloid peptide of different length. In each case, the ordinate shows the percentage intensity (% Int.) corresponding to each one of the peaks of different mass (Mas.), deduced from the mass/charge ratio (m/z). The top graph, indicated with the letter A and marked "Ctrl." on the right, was obtained from a solution that contained the peptides comprising amino acids 12 to 29 (Pep. Aβ. 12-29), 1 to 40 (Pep. Aβ. 1-40) and 1-42 (Pep. Aβ 1-42) of β-amyloid peptide. The bottom graph, indicated with the letter B and marked "EM5+PM" on the right, was obtained after concentration of the peptides from the solution containing them by using the EM5 antibody bound covalently to magnetic particles and separation of the complexes formed by the use of a magnetic field. The drawing at bottom right represents the binding region of the antibody to each of the peptides under consideration.

Figure 7:
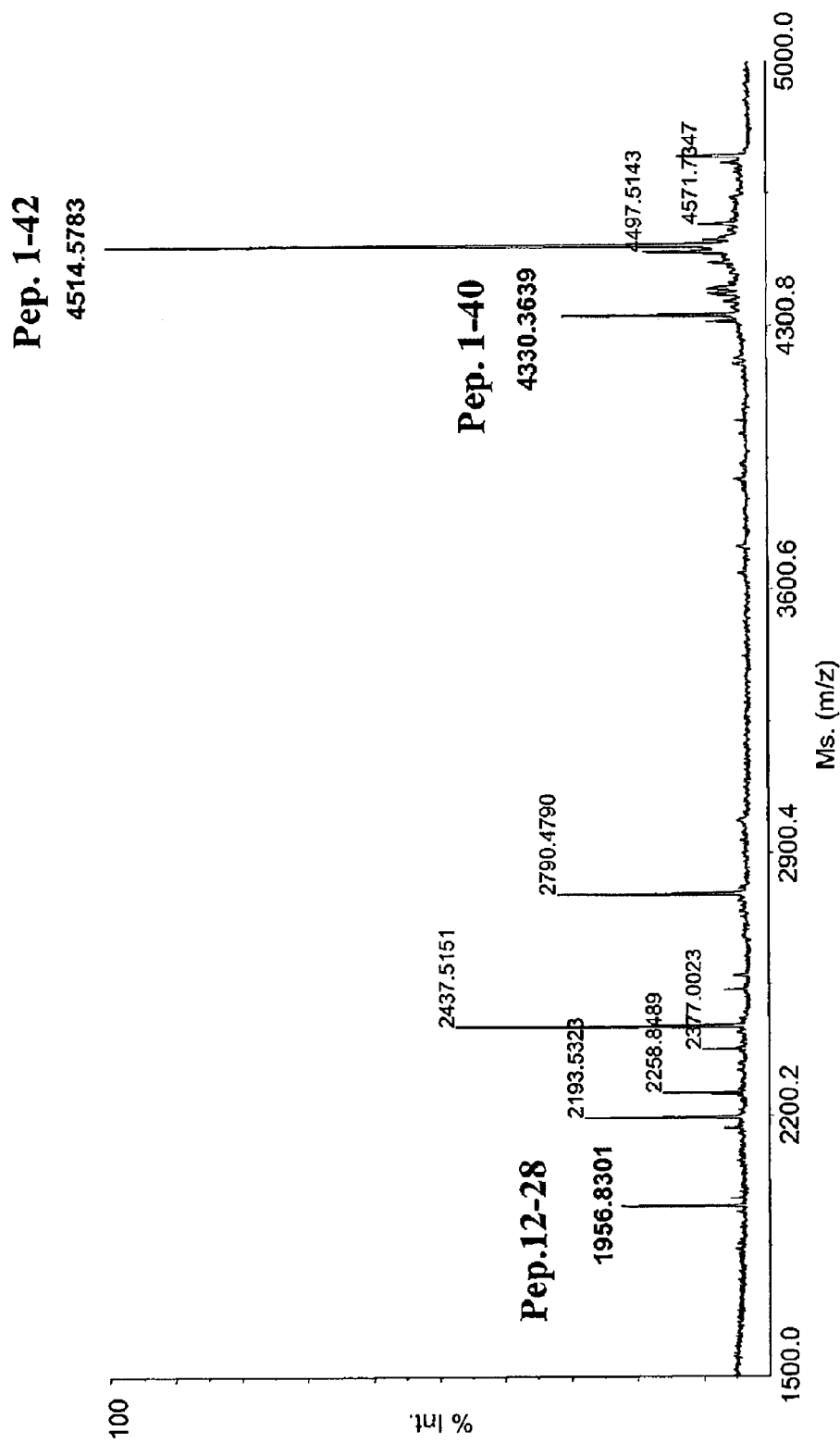

FIG. 7 shows a graph obtained by analysis by MALDI-TOF mass spectrometry of a urine sample from a healthy individual to which additional quantities of the peptides that comprise amino acids 12 to 28 (peak marked as Pep. 12-28), 1 to 40 (peak marked as Pep. 1-40) and 1-42 (peak marked Pep. 1-42) of β-amyloid peptide had been added, after which the sample was treated with the EM5 antibody bound covalently to magnetic particles and the complexes that formed were separated by applying a magnetic field. The ordinate shows the percentage intensity (% Int.) corresponding to each of the peaks of different mass (Ms.), deduced from the mass/charge ratio (m/z). The peaks corresponding to each of the forms of β-amyloid peptide added to the urine sample are indicated.

DETAILED DESCRIPTION OF THE INVENTION

As already mentioned, the invention relates to a monoclonal antibody, EM5, that recognizes, in β-amyloid peptide, the epitope corresponding to the sequence:
Val-His-His-Gln-Lys (SEQ ID NO:3)
This sequence corresponds to that of residues 12-16 of human β-amyloid peptide. Consequently, it is to be hoped that the aforesaid antibody would be capable of binding to isoforms of β-amyloid peptide that contained said sequence, without recognizing those that lacked it, for example the so-called p3 peptide ($A\beta_{17-42}$) and other forms with the amino end truncated ($A\beta_{17-X}$). In the characterization of the monoclonal antibody that is described in detail in the examples given below it is demonstrated that EM5 binds to any peptide containing residues 12 to 16 of the sequence of human Aβ, even though it has modifications outside of this region, and it does not recognize peptides which lack said region. If the region is modified, as is the case with peptide $A\beta_{1-28}$ (rodent), which has a change of amino acid in position 13, as well as in positions 5 and 10, the peptide is no longer recognized by EM5.

Moreover, studies show that the antibody is capable of binding to isoforms of the Aβ peptide that contain residues 12 to 16 regardless of whether they are in soluble form, in aggregated form, or denatured (in SDS). In particular, the tests described in the Examples that are presented below show that the antibody of the invention is capable of binding both to isoforms of β-amyloid peptide that have aggregated, forming a proportion of the plaques present in samples of brain tissue, and to isoforms of β-amyloid peptide that are in solution, including when the solution is a sample of biological fluid such as urine. Therefore, another aspect of the invention relates to a composition that contains the antibody of the invention, or at least one fragment thereof capable of binding to SEQ ID NO:3, coupled to a substance that permits its detection and/or its concentration, and to its use in the diagnosis of Alzheimer's disease.

When the antibody of the invention or a fragment thereof is coupled to a substance that permits it to be detected, detection of the presence of the isoforms of β-amyloid peptide that have bound to the antibody or a fragment thereof and/or the quantification thereof will be possible by detection and/or quantification of the antibody or fragment thereof bound to isoforms of β-amyloid peptide that contain the specific sequence recognized by the antibody of the invention. In a preferred embodiment of the invention, the substance to which the antibody, or a fragment thereof capable of binding to SEQ ID NO:3, is coupled is a second antibody capable of binding to the monoclonal antibody of the invention, the second antibody being bound to an enzyme capable of catalyzing the conversion of a particular substance to another that possesses characteristics that facilitate detection of its presence. In the most preferred embodiment of the invention, the second antibody bound to an enzyme is part of the Envision system, from Dako Laboratories, the substance whose conversion is catalyzed by the enzyme being a chromogen and the enzyme that catalyzes the reaction being either alkaline phosphatase (in that case using nitroblue tetrazolium as chromogen) or horseradish peroxidase (in that case using diaminobenzidine as chromogen).

Another possibility is that the antibody of the invention or a fragment thereof is bound to a substance or particle that facilitates concentration of the isoforms of β-amyloid peptide that have become bound to said antibody or a fragment thereof. This embodiment is preferred when the composition of the invention is to be used for the detection and/or quantification of isoforms of β-amyloid peptide that are present in solution, especially in a solution in which their concentration is low, such as blood or plasma, urine or cerebrospinal fluid. The substance or particle will be such as permits easy separation of the antigen-antibody complex from said solution, for example by immunoprecipitation. A preferred example of said particles are magnetic particles which, when coupled to the antibody of the invention or to a fragment thereof capable of binding to isoforms of β-amyloid peptide that contain the specific sequence recognized by the antibody of the invention, will permit the isoforms of β-amyloid peptide bound to the antibody or to a fragment thereof to be extracted from the solution if a suitable magnetic field is applied. Subsequently, the isoforms of β-amyloid peptide can be separated from the antibody or fragment thereof and can then be detected, identified and/or quantified. A method that is suitable is mass spectrometry, especially that known as MALDI-TOF (Matrix Assisted Laser Desorption Ionization Time-of-flight).

As already mentioned, the antibody of the invention or a fragment thereof capable of binding to isoforms of β-amyloid peptide that contain the specific sequence recognized by the antibody of the invention, as well as the compositions that contain at least one of them, can be used for the in-vitro diagnosis of Alzheimer's disease. The methods of in-vitro diagnosis of Alzheimer's disease that make use of the antibody of the invention or of a fragment thereof capable of binding to isoforms of β-amyloid peptide that contain the specific sequence recognized by the antibody of the invention, as well as those that make use of compositions that include said antibody or said fragment, are within the scope of the invention. Said diagnosis can be carried out on brain tissue, in which the presence of deposits in which isoforms of the amyloid peptide that contain the sequence recognized by the monoclonal antibody of the invention predominate (neuritic plaques and vascular deposits, deposits that are characteristic of the development of Alzheimer's disease) is revealed selectively, detecting the existence of binding, to said deposits, of the monoclonal antibody of the invention, or of a fragment thereof capable of binding to the specific sequence recognized by said antibody, in contrast to what will occur with the deposits in which the predominant isoforms are those that lack the sequence recognized by the monoclonal antibody of the invention (diffuse plaques), the isoforms $A\beta_{17-X}$, which would not exhibit binding of the monoclonal antibody or of fragments thereof. Binding of the antibody to neuritic plaques and vascular deposits is revealed by means of a composition such as one of those that comprise, in addition to the antibody of the invention or a fragment thereof, a second antibody capable of binding to the monoclonal antibody of the invention, the second antibody being bound to an enzyme capable of catalysing the conversion of a defined substance to another that possesses characteristics that facilitate the detection of its presence, such as a chromogen. In the most preferred embodiment of the diagnostic technique of the invention on brain tissue, the method of diagnosis is supplemented with the additional use of the polyclonal antibodies EM2 and EM3, which recognize either $A\beta_{X-42}$ (EM3) or $A\beta_{X-40}$ (EM2), both antibodies also having been developed previously by the group of authors of the invention [24].

Another embodiment of the method of diagnosis of the invention is carried out on a biological fluid that is known to contain isoforms of β-amyloid peptide, such as cerebrospinal fluid, urine or blood or, in this last-mentioned case, plasma derived therefrom. Since puncture is required to obtain cerebrospinal fluid, it is preferable to use plasma or urine, and especially the latter, which can be obtained without the use of invasive techniques. It is then preferred that the method of diagnosis of the invention should employ compositions that comprise the antibody of the invention or a fragment thereof bound to some substance or particle that facilitates the concentration of the isoforms of β-amyloid peptide that bind to said antibody or to a fragment thereof. As already mentioned, the particles that facilitate the concentration of the isoforms of β-amyloid peptide are preferably magnetic particles coupled to the antibody or to a fragment thereof, so that when the solution that contains the complexes formed with the isoforms of β-amyloid peptide is submitted to the action of a magnetic field, the latter can be extracted from the solution, which can easily be discarded using a method such as aspiration. In the case when a complete antibody is used, it is especially preferable for coupling of the antibody to the magnetic particle to be effected by a covalent bond, to increase its stability, but establishment of said covalent bond in such a way as to avoid, as far as possible, the antigen binding site, so as not to diminish the binding capacity of the antibody, therefore methods are preferred in which binding takes place preferentially in the histidine-rich zone of the Fc fragment of the antibody or in the glycoside chains of said zone. In this connection, the method of binding of the antibodies to magnetic particles described by Fuentes et al. [26] is particularly preferred.

Once the binding complexes of the isoforms of β-amyloid peptide have been separated from the solution, separation of said isoforms of the antibodies or of the fragments thereof is preferable prior to detection and/or quantification of the isoforms of β-amyloid peptide extracted, for which acetonitrile and trifluoroacetic acid can be used. Since the concentration of isoforms of β-amyloid peptide in urine is usually quite low, detection and/or quantification are preferably carried out using a very sensitive method such as MALDI-TOF mass spectrometry.

Another aspect of the invention is a hybridoma cell line capable of producing the monoclonal antibody of the invention. In a preferred embodiment of the invention, said cell line is obtained by fusion, with the mouse myeloma line P3/X63-Ag.653, of spleen cells from BALB/c mice immunized with peptide $A\beta_{1-40}$ coupled to KLH (keyhole limpet haemocyanin).

Finally, yet another aspect of the invention is a method of production and purification of the monoclonal antibody of the invention starting from hybridoma cells. In the preferred embodiment of the invention, the method comprises production of a hybridoma cell line as described previously and growing it as ascitic fluid in BALB/c mice treated beforehand with Pristane. The monoclonal antibody is purified from this ascitic fluid by affinity chromatography in a column of Protein A-Sepharose (Pharmacia). In a particularly preferred embodiment of the invention, the hybridoma cells employed are from the line designated "EM5 clone A", deposition of which was requested on 1 Mar. 2006 in the European Collection of Cell Cultures (ECACC). CAMR, Porton Down, Salisbury, Wiltshire, United Kingdom, and was given the access number 06030101.

The invention and its preferred embodiments are now described in more detail using the following examples.

EXAMPLES

Example 1

Production of Antibodies

The polyclonal antibodies EM2 and EM5 used in this study were produced in the manner reported previously [24].

The following steps were carried out for production of the EM5 monoclonal antibody:

Production of Hybridomas

BALB/c mice were injected subcutaneously with 40 μg of peptide $A\beta_{1-4}$ coupled to KLH (keyhole limpet heamocyanin) and dissolved in phosphate-buffered saline (PBS) and emulsified with an equal volume of Freund complete adjuvant. The mice received three injections repeated every other week, in Freund incomplete adjuvant. Three days before fusion, the mice received an intraperitoneal injection of 25 μg of $A\beta_{1-40}$-KLH in PBS. On the day of fusion, spleen cells from animals immunized with the mouse myeloma line P3/X63-Ag.653 were fused using polyethylene glycol 1400 (Sigma), following established procedures [25]. The fused cells were distributed in sterile 96-well plates at a density of 105 cells per well and were selected in media containing hypoxanthine, thymidine and aminopterin. The antibody-producing hybridomas were identified by ELISA, described later.

Screening of Hybridomas.

Polystyrene microtitre plates (Maxisorb, Nunc) were covered overnight at 4° C. with $A\beta_{1-40}$ at 5 μg/ml in carbonate buffer 50 mM, pH 9.6 (covering buffer). The plates were washed with Tween 20 at 0.05% in PBS (PBS-T) and the nonspecific binding sites were blocked with bovine serum albumin (BSA) at 2% in PBS-T (blocking solution) for 1 hour at 37° C. After washing, the plates were incubated for 1 hour with tissue culture supernatant diluted twice in blocking solution. The plates were washed again and were incubated with goat anti-mouse IgG conjugated with horseradish peroxidase (Sigma) for 1 hour at 37° C. After washing, the substrate (0.05% o-phenylenediamine and 0.015% hydrogen peroxide in citrate buffer 100 mM, pH 5.0) was added to the solution. The reaction was stopped 10 minutes later with 2.5 M sulfuric acid and the absorbance at 492 nm was determined in a microplate reader. The hybridomas whose supernatants produced an absorbance value at least twice that obtained with the supernatant from unrelated hybridomas (anti-gliadin antibodies) were selected. The hybridomas that produced specific antibodies were cloned repeatedly using limiting dilution, and the isotypes of the monoclonal antibodies were determined in cell culture supernatant concentrated by gel immunoprecipitation using a specific antiserum (Sigma). The selected hybridomas were grown as ascitic fluid in BALB/c mice previously treated with Pristane.

Purification of Monoclonal Antibodies.

The EM5 monoclonal antibody was purified from the ascitic fluid by affinity chromatography in a column of Protein A-Sepharose (Pharmacia). The purified antibodies were dialyzed profusely in PBS and were stored at −85° C. until they were used.

Example 2

Calculation of the Apparent Dissociation Constant: Affinity for Peptides $A\beta_{1-40}$ and $A\beta_{1-42}$ ELISA was used for investigating the affinity of EM5 and 6E10 monoclonal antibodies using recently dissolved, immobilized peptides Aβ$_{1-40}$ and Aβ$_{1-42}$, which had been synthesized in the WM Keck plant of Yale University using the N-t-butyloxycarbonyl methodology.

Polystyrene microtitre plates (Immulon 2, Dynex Technology Inc., Chantilly, Va.) were covered for 16 hours at 4° C. with 0.5 μg of peptide Aβ$_{1-40}$ or Aβ$_{1-42}$ recently dissolved or aggregated in carbonate/bicarbonate buffer pH 9.6. After blocking with Superblock (Pierce Chemical Co.), increasing concentrations of purified EM5 (0-0.5 nM in TBS-T, 100 microliters per well) were added to the wells covered with Aβ, incubating for 3 hours at 37° C. The bound EM5 was detected with the F(ab')2 fragment of goat anti-mouse IgG conjugated with horseradish peroxidase (1:3000, Amersham). The reaction was developed for 15 minutes with 3,3',5,5'-tetramethylbenzidine (TMB) (BioRad, Hercules, Calif.), it was stopped with 2M sulfuric acid and was quantified in a microplate reader (Cambridge Technology, Watertown, Mass.) at 450 nm. The affinity of the commercially available antibody 6E10 (Senetek, PLC) was investigated following a similar protocol using preparations of purified IgG antibodies. Nonlinear regression analysis, estimation of apparent dissociation constants and comparison of protein binding data for finding the statistical significance by calculating the F ratios were evaluated using Prism software from (GraphPad (GraphPad, San Diego, Calif.).

FIG. 1 shows saturation curves corresponding to binding, in ELISA, of EM5 and 6E10 monoclonal antibodies to recently dissolved and aggregated Aβ peptides. High affinity was observed in all cases, with apparent dissociation constants in the picomolar range. None of these antibodies displayed differential affinity for recently prepared or aggregated forms of Aβ. Interestingly, whereas 6E10 displayed equivalent affinity for A Aβ$_{1-40}$ and Aβ$_{1-42}$, EM5 displayed greater affinity for Aβ 42 than for Aβ 40 (p<0.01) (13.7 pM and 15.5 pM for recently prepared and aggregated Aβ 42, respectively; and 37.5 pM and 37.0 pM for recently prepared and aggregated Aβ 40, respectively).

Example 3

Immunotransfer Analysis

The specific recognition of Aβ$_{1-40}$ and Aβ$_{1-42}$ by EM5 was investigated and compared with EM2 and EM3 polygonal antibodies by means of immunotransfer analysis. For this, Aβ peptides (0.5 μg/lane) were submitted to PAGE electrophoresis in 16% acrylamide, tris-tricine-SDS. The peptides were transferred electrophoretically for 1 hour at 400 mA and 4° C. to poly(vinylidene fluoride) membranes (Immobilon-P, Millipore) using 3-cyclohexylamino-1-propanesulfonic acid, pH 11, containing 10% methanol. The membranes were blocked for 16 h at 4° C. with TBS-T containing 5% powdered skimmed milk and were then incubated for 1 hour at room temperature with 2 μg/ml of IgGs EM2, EM3 or EM5. A goat anti-rabbit IgG (EM2 and EM3) or goat anti-mouse IgG (EM5) coupled to horseradish peroxidase (Amersham) and diluted 1:2000 was used as the second antibody. Immunotransfer was visualized by means of chemoluminescence (Amersham) following the manufacturer's specifications.

Figure 2:
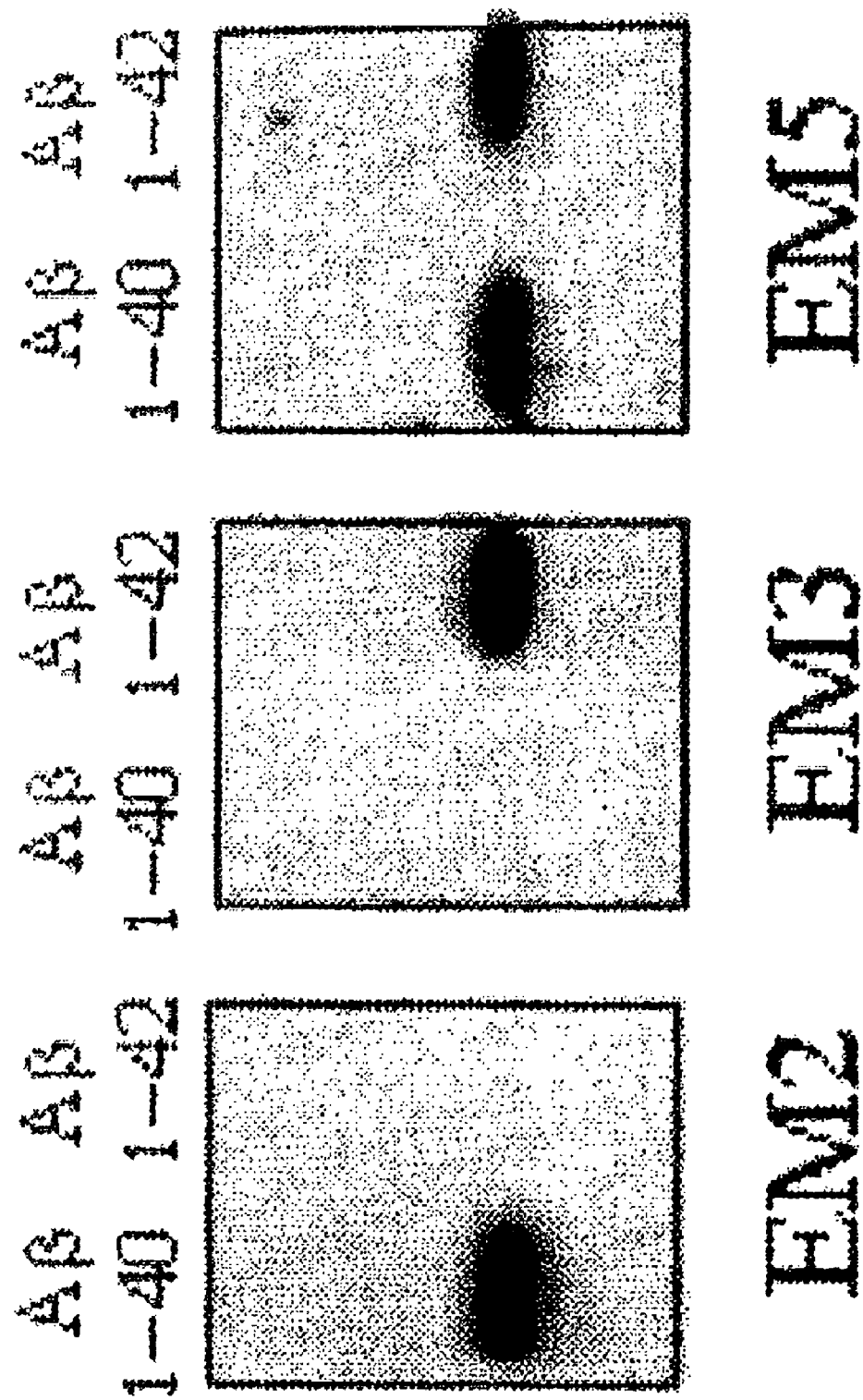
FIG. 2 shows the result from immunotransfer analysis of the antibodies EM2, EM3 and EM5 relative to synthetic peptides Aβ 1-40 and Aβ 1-42.

The results are shown in FIG. 2, where it can be seen that, in the immunotransfer experiments, EM5 displayed immunoreactivity both to Aβ$_{1-40}$ and Aβ$_{1-42}$ peptides (corroborating the results obtained by ELISA), whereas antibodies EM2 and EM3 were only able to recognize peptides Aβ$_{1-40}$ or Aβ$_{1-42}$, respectively, as described previously [24]. These results support the notion that the EM5 monoclonal antibody binds to a specific linear epitope common to both peptides, which is conserved in the samples treated with SDS. Overall, our results show that EM5 is able to recognize Aβ peptides in the soluble form, aggregated form and denatured form (in SDS), with slightly preferential binding to Aβ 42, probably as a result of the increase in hydrophobicity of the peptide.

Example 4

Localization of the Epitope

For precise localization of the exact epitope recognized by the EM5 antibody, binding of the antibody to a series of synthetic Aβ peptides was analyzed. Peptides Aβ$_{1-16}$, Aβ$_{1-28}$ and Aβ$_{25-35}$ were obtained from Sigma (San Luis, Mo.); peptides Aβ$_{1-42}$, Aβ$_{1-42}$ (E22Q), Aβ$_{1-40}$, Aβ$_{1-40}$ (E22G), Aβ$_{1-40}$ (E22Q), Aβ$_{1-28}$ (rodent), Aβ$_{1-28}$ (E22Q), Aβ$_{17-40}$, Aβ$_{16-42}$ and Aβ$_{16-42}$ were synthesized in the WM Keck plant of Yale University using the N-t-butyloxycarbonyl methodology; Aβ$_{21-28}$, Aβ$_{21-28}$ (E22Q), Aβ$_{37-41}$ and Aβ$_{37-40}$ were synthesized in the Peptide Synthesis Unit (National Biotechnology Center, Madrid) using ordinary Fmoc methodology. The design of peptides Aβ$_{37-42}$ and Aβ$_{37-49}$ included a tail at the amino end with a cysteine residue for coupling which had the sequence CSGGSGGG (SEQ ID NO:4). All the peptides were purified by high-performance liquid chromatography in inverted-phase mode and their purity was evaluated by MALDI-TOF mass spectrometry.

a) Antibody-Capture ELISA

To carry out the test, flat-bottomed polystyrene microtitre plates (Immulon 2, Dynex Technology Inc., Chantilly, Va.) were covered for 16 hours at 4° C. with 1 μg/well of the corresponding Aβ peptide in carbonate-bicarbonate buffer 0.1 M, pH 9.6. After blocking with NaCl 150 mM, Tris 20 mM, Tween-20 at 0.05%, pH 7.4 (TBST) containing 2% BSA, series dilutions of the EM5 antibody (from 20 to 0.02 mg/ml of the IgG fraction) were incubated for 1 hour at 37° C. Anti-mouse IgG coupled to peroxidase (Sigma, San Luis, Mo.) and diluted 1:2000 was then applied for 30 minutes at 37° C. The reaction was developed with TMB (BioRad, CA), stopped with 2M sulfuric acid and quantified at 450 nm. Nonspecific binding was determined, omitting the first antibodies.

Figure 3:
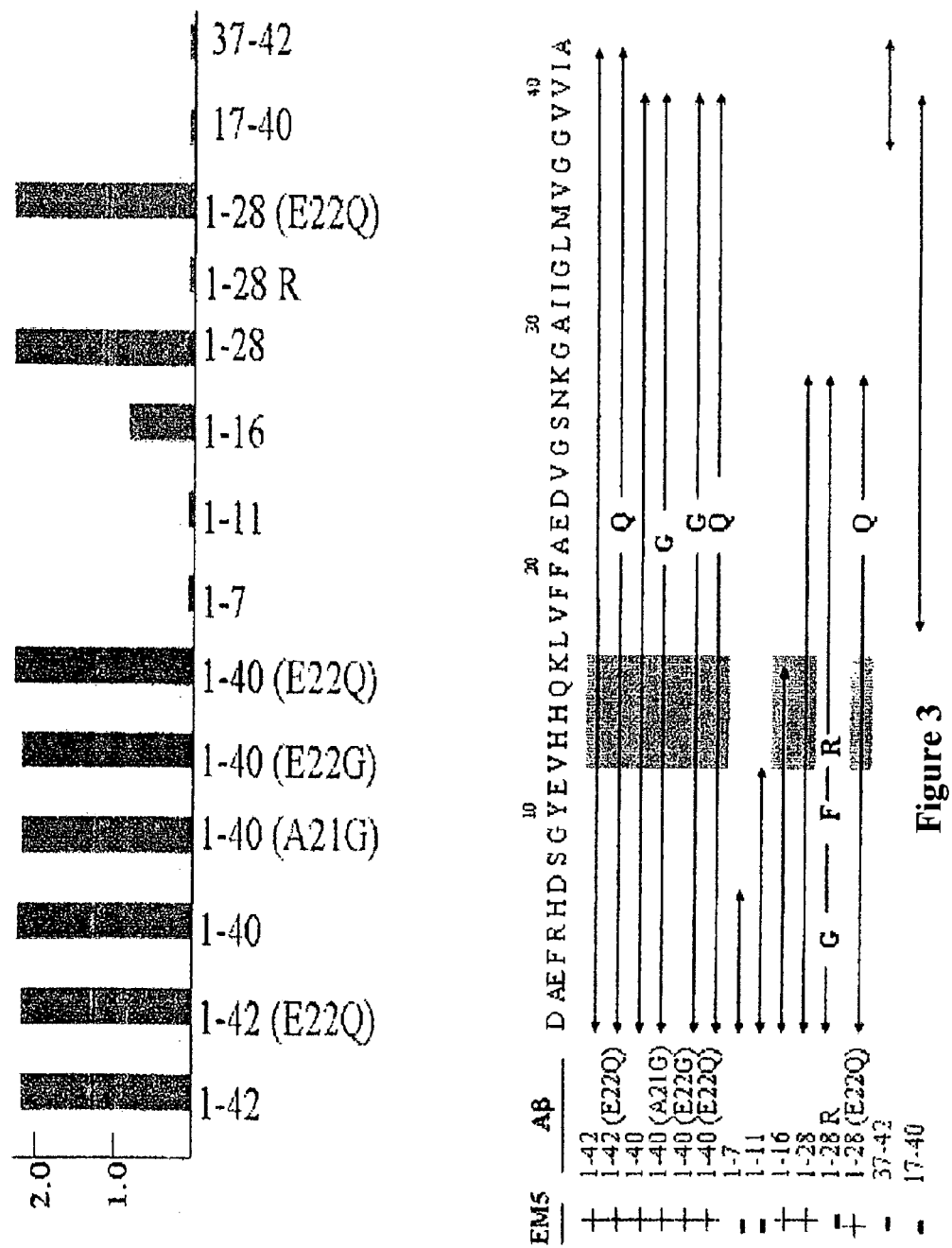
FIG. 3 shows, at the top, a bar chart for the reactivity of EM5 to series of synthetic Aβ peptides by means of ELISA, with the values of absorbance (O.D. al 450 nm) corresponding to 20 µg/ml of antibody. The bottom part shows the localization of the epitope recognized by EM5 according to the results obtained in this ELISA 1-28R=rodent $A\beta_{1-28}$. In parentheses, various mutations.

The results are presented in FIG. 3, the top part of which shows a bar chart corresponding to the absorbance values obtained corresponding to incubation of 20 μg/ml of the antibody with each of the peptides. EM5 was shown to bind to any peptide that contained residues 12 to 16 of the sequence of human Aβ and was unable to recognize peptides lacking this region. Moreover, mutant variants with modifications outside of this region (Aβ$_{1-42}$ (E22Q), Aβ$_{1-40}$ (A21G), Aβ$_{1-40}$ (E22G), Aβ$_{1-40}$ (E22Q)) displayed similar binding when compared with the wild-type peptide, whereas the Aβ$_{1-28}$ (rodent) peptide, which shows three changes of amino acids in positions 5, 10 and 13, was not recognized by EM5.

b) Mass Spectrometry Analysis of Digested and Immunoprecipitated β-Amyloid Peptide To confirm the results, an additional study was conducted in which a set of peptides derived from Aβ$_{1-42}$, generated by digestion with trypsin or α-chymotrypsin, was brought into contact with magnetic particles coated with EM5 antibody, carrying out the following steps:

For digesting the peptide, 0.5 μl of trypsin or α-chymotrypsin containing 0.025 μg of the enzyme was added to a 10 μl aliquot of β-amyloid peptide in ammonium bicarbonate 50 mM containing 1 μg of peptide. Incubation was carried out for 2 hours at 37° C. The digestions carried out are shown schematically in Table 1.

For immobilizing the EM5 monoclonal antibody on magnetic particles, a 5 µl aliquot (1.1 mg/ml) of EM5 was incubated with 50 µl of Dynabeads M450 coated with goat anti-mouse IgG at room temperature for 2 hours. The complex was washed 4 times with PBS with bidirectional stirring (in a rotor).

To perform immunoprecipitation, a 10 µl aliquot of β-amyloid peptide digested with trypsin (or α-chymotrypsin) with 50 µl of EM5 immobilized on magnetic particles was incubated in a rotor for 1 hour at 37° C. The magnetic-immunoprecipitate complex was washed 4 times with PBS in the same rotor and the supernatants were aspirated and discarded.

For mass spectrometry analysis of digested immunoprecipitated β-amyloid peptide, the immunoprecipitated peptides contained in the magnetic complexes were released with 20 µl of 50% acetonitrile/0.3% trifluoroacetic acid. 5 µl of this solution was mixed with 5 µl of saturated α-cyano-4-hydroxycinnamic acid in 0.1% trifluoroacetic acid/acetonitrile (2:1). A volume of 0.5 µl of this solution was then placed in a pointed stainless steel probe and was left to dry at room temperature. The samples were measured in a MALDI-TOF mass spectrometer Reflex II from Bruker equipped with an ion source with visualization optics and an $N_2$ laser (337 nm). The mass spectra were recorded in positive linear mode at an accelerating voltage of 28.5 kV and 1.5 kV in the linear detector, accumulating 200 laser single-shot spectra below the irradiance threshold. Only mass signals with good resolution, of high intensity, emitted from 3-5 selected points of incidence, were taken into account. All the MALDI spectra were calibrated externally using a standardized mixture of peptides [angiotensin II (1047.2), 18-39 fragment of adrenocorticotropic hormone 2466.7) and insulin (5734.6); Sigma].

The characteristics of the peptides analyzed, as well as the data obtained, are summarized in the following Table 1:

TABLE 1

MALDI-TOF mass spectrometry data for fragments obtained by digestion of β-amyloid peptide

| Fragment N° | Amino acids included | Enzyme used | Experimental mass (m/z) | Expected value (m/z) |
| --- | --- | --- | --- | --- |
| 1 | 1-16 | Trypsin | 1956.57 | 1955.0 |
| 2 | 1-17 | α-Chymotrypsin | 2067.37 | 2068.2 |
| 3 | 5-17 | α-Chymotrypsin | 1606.62 | 1605.7 |
| 4 | 6-16 | Trypsin | 1337.12 | 1336.4 |
| 5 | 11-17 | α-Chymotrypsin | 888.66 | 890.0 |

Figure 4:
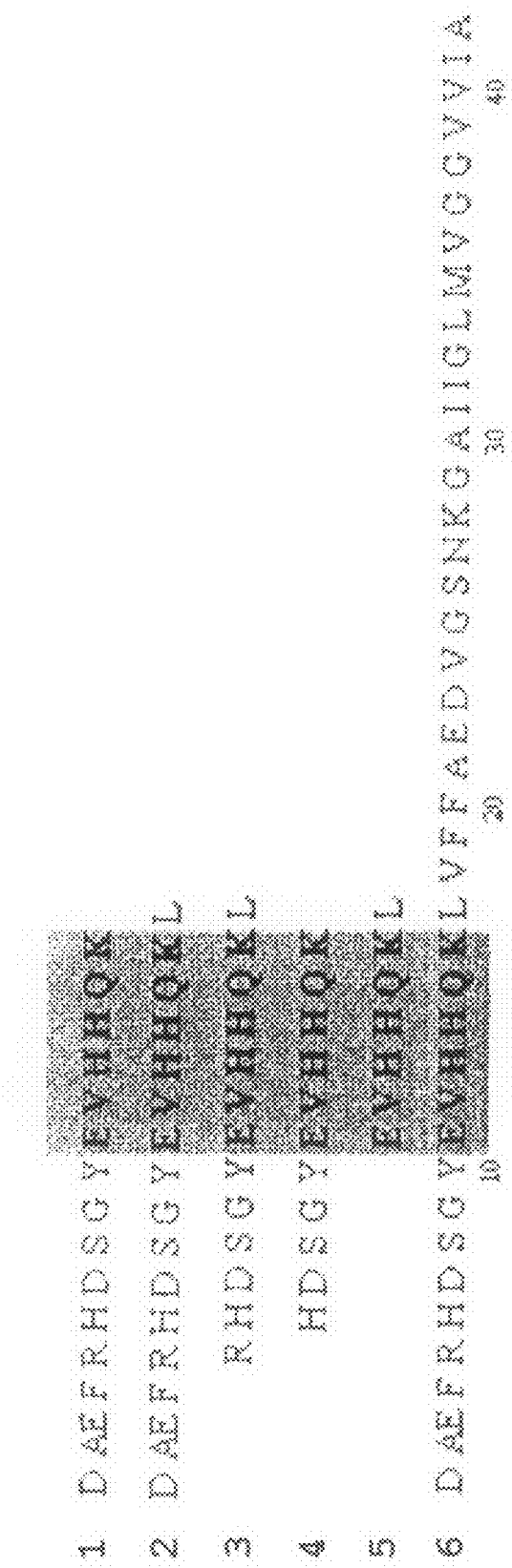
FIG. 4 shows the localization of the epitope of the Aβ peptide recognized by the EM5 monoclonal antibody as determined by analysis by mass spectrometry of immunoprecipitated β-amyloid peptide digested with various proteolytic enzymes given in the table in the description (peptides 1-5). Sequence 6 corresponds to β-amyloid peptide without digestion.

The sequences of each of these peptides (1-5) and of the peptide without digestion (6) are shown in FIG. 4, in which the zone that appears to correspond to the epitope recognized by the EM5 antibody according to the results of MALDI-TOF mass spectroscopy of the immunoprecipitated material is shaded.

As can seen in said FIG. 4, analysis of the immunoprecipitated material by MALDI-TOF mass spectroscopy shows that EM5 was capable of extracting, from the digestion mixture, each fragment of peptide that contained residues 11-16 (shaded regions). Fragments of peptide outside of this region were not recovered from the solution. These results confirm the data obtained by ELISA and immunotransfer analysis.

In conclusion, the differential reactivity of the antibody to a series of AO peptides indicates that EM5 recognizes residues 11-16 of Aβ peptides. Among them, participation of residues 12-16 is fundamental, as is demonstrated by the fact that mutation of residue 12 in the rodent $A\beta_{1-28}$ peptide (1-28 R) inhibits its recognition by the antibody; for its part, involvement of residue 11 (E) in the conformation of the epitope cannot be ruled out, although the data obtained do not fully confirm it.

Example 5

Immunohistochemistry: Tissue Reactivity of the Antibodies

To demonstrate the validity of the EM5 antibody for revealing deposits that are characteristic of Alzheimer's disease (neuritic plaques and vascular deposits) as opposed to diffuse plaques, immunostaining of sections of brain tissue affected by Alzheimer's disease was performed using the antibodies EM2 (a polyclonal antibody directed at the carboxyl end of the Aβ 40 peptide), EM3 (a polyclonal antibody directed at the carboxyl end of the Aβ 42 peptide) and EM5 (a monoclonal antibody with demonstrated specificity for residues 12-16 of the Aβ peptide). Both EM2 and EM3 were used in an earlier study [24].

Processing of Brain Tissue and Areas Selected for Immunohistochemistry.

The brain tissue was supplied by the Tissue Bank for Neurological Investigations, Madrid. Six subjects, 3 men and 3 women, with well-defined AD were included in the study. Their ages ranged from 68 to 75 years. In all cases the diagnosis of AD was based on the clinical-pathological guidelines of CERAD (*Consortium to Establish a Registry for Alzheimer's Disease*) [10]. None of the patients had other relevant neuropathologic findings, for example Parkinson's disease or significant vascular changes. All the brains were processed for histological examination following the protocols for cutting, fixation and embedding of the Brain Bank. The periods post-mortem varied between 10 and 18 hours. Immediately after autopsy one half of the brain (obtained by medio-sagittal section of the cerebral hemispheres, cerebellum and brain stem) was fixed in formaldehyde buffered with 4% phosphate. After fixation for 3-4 weeks, blocks of tissue were obtained from all the cortical and subcortical areas with significant involvement in AD, and were embedded in paraffin after gradual dehydration in ethanol and clarification of the tissue with xylene. In all cases, 5 µm tissue sections, corresponding to the parieto-occipital lateral cortex, temporal lateral cortex (these last two areas as recommended by the CERAD guidelines [10]), hippocampus, caudatum—putamen (at the head of the caudate nucleus), and cortex of the cerebellar hemisphere, were obtained from the original paraffin blocks for immunohistochemical examination. As control of nonspecific amyloid staining, modified methenamine—silver staining was carried out in sections consecutive to those processed for the amyloid immunohistochemistry.

Antibodies and Immunostaining Protocols

The primary antibodies employed were EM2, EM3, and EM5. Both EM2 and EM3 were used in an earlier study [24]. The sections were incubated with primary antibodies at room temperature for 30 minutes. The polyclonal antibodies were detected with the Envision system (Dako Laboratories) with alkaline phosphatase (APh) using nitroblue tetrazolium (NET) as chromogen, and EM5 was detected either with the aforementioned system or with the Envision system (Dako Laboratories) with horseradish peroxidase (HRP) using diaminobenzidine (DAB) as chromogen. In the case of colocalization techniques, the polyclonal antibodies were always detected with the Envision system with APh (using NBT as chromogen), whereas EM5 was detected with the Envision system with HRP (using DAB as chromogen).

Double and Single Immunostaining.

Double immunostaining techniques were employed, using EM5 as first primary antibody and EM2 or EM3 as second primary antibody, as a preliminary operation for the purpose of establishing the degree of colocalization of each pair of antibodies, together with the optimum working dilution of each of them. During this phase of the study, which was restricted to tissue sections from the parieto-occipital cortex of two of the cases, it was established that the use of EM5 as first primary antibody ruled out a masking effect of the other two antibodies, when they were employed as first antibody during the double immunostaining technique. In serial sections from both selected paraffin blocks, increasing dilutions (1:50, 1:100, 1:500, 1:1000 and 1:2000) of EM5 were colocalized with decreasing dilutions (1:2000, 1:1000, 1:500, 1:100 and 1:50) of EM2 or of EM3. As it was found that the EM2 antibody was colocalized to a high degree with EM5, the rest of the study aimed to demonstrate the differential pattern of reactivity displayed by EM5 and EM3. For this purpose, subsequent double immunostaining in sections of all the selected areas was limited in all cases to the use of EM5 (at 1:1000 dilution) as first primary antibody and EM3 (at 1:1000 dilution) as second primary antibody. In addition, for more accurate visualization of the pattern of reactivity displayed by each antibody in the same tissue, single immunostaining was carried out in serial sections from each block using EM5, EM2 or EM3 as primary antibody. As the main purpose of this part of the study is to compare qualitatively different patterns of immunoreactivity, rather than quantitative differences between antibodies, the results of the stainings were not quantified.

Results

Figure 5:
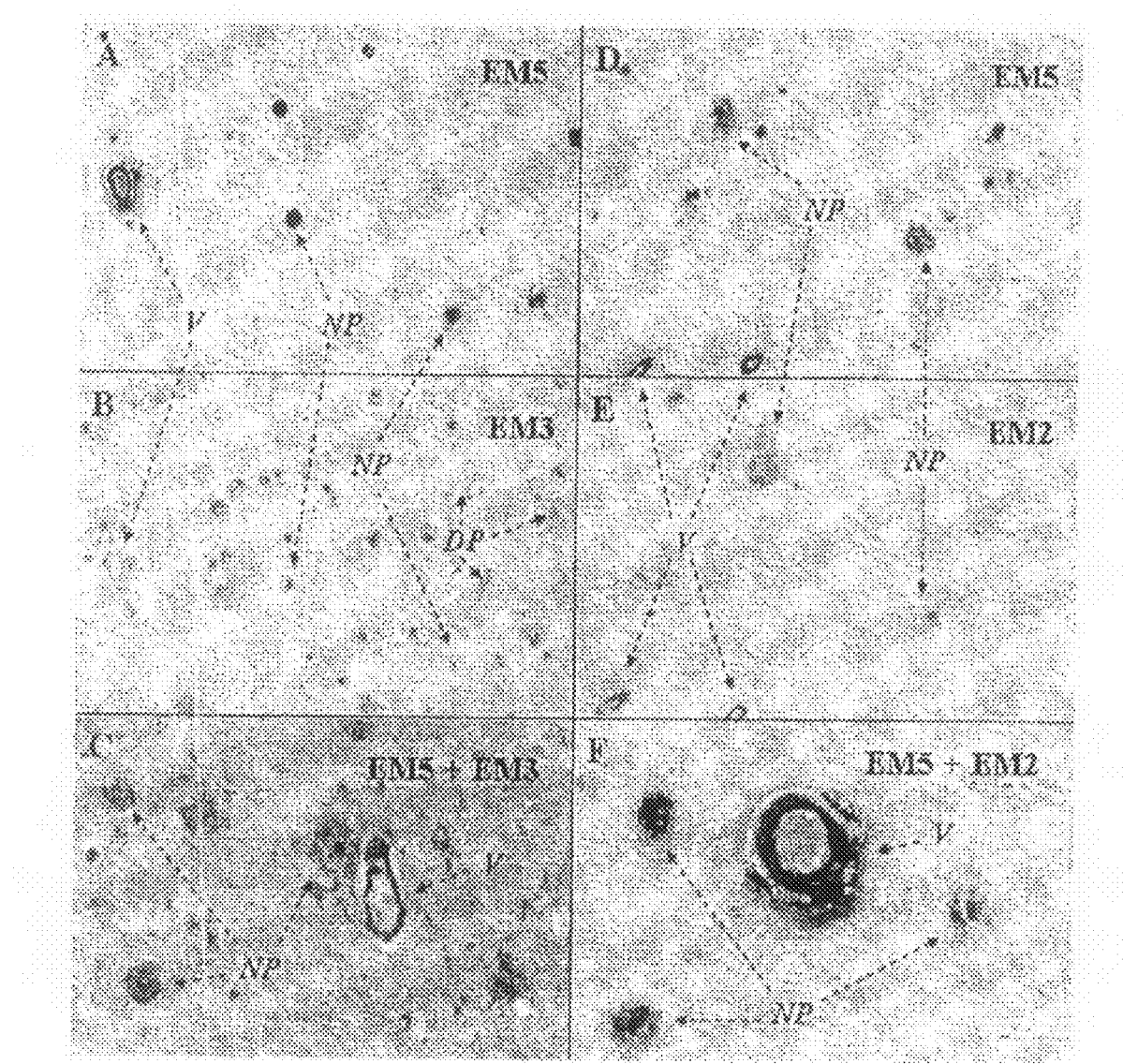

The results from one of the cases can be seen in FIG. 5, presented with the distribution mentioned previously, i.e.:

(A) and (B): Consecutive serial sections from the same zone of the occipital cortex immunostained with EM5 (A) and EM3 (B) as primary antibody, using NBT as chromogen. The vessels (V) are labelled to facilitate localization of the plaques. Whereas EM3 (B) reveals both diffuse plaques (DP) and neuritic plaques (NP), as well as deposits in the blood vessels (V), EM5 (A) gives more intense staining both of blood vessels and of some neuritic plaques, although not diffuse plaques.

(C) Micrograph at high magnification of a double immunostaining technique using EM3 (using NBT—blue color—as chromogen) and EM5 (using DAB—brown color—as chromogen) as primary antibodies. Double immunostaining of the neuritic plaques and the wall of the vessels is observed.

(D) and (E): Consecutive serial sections of the same area of the occipital cortex immunostained either with EM5 (D) or with EM2 (E). Once again, the vessels (V) have been labelled to assist in identifying the plaques. It can be seen that both the vessels and the neuritic plaques react with both antibodies. Fewer neuritic plaques are stained with EM2 than with EM5, and no diffuse plaque reacts with either of them.

(F) Microphotograph at high magnification of a double immunostaining technique using EM2 (using NBT—blue color—as chromogen) and EM5 (using DAB—brown color—as chromogen) as primary antibodies in the same section of tissue from the occipital cortex. Precise colocalization of the reactivity of both antibodies in the vessel wall and the neuritic plaques is observed.

All cases except one show pronounced leptomeningeal and intracortical vascular amyloid deposits which reacted with all the antibodies tested. In all positive cases the immunoreactivity of the vascular amyloid deposits was more pronounced (more extensive and more intense) both with EM2 (FIG. (5E)) and with EM5 (FIGS. (5A) and (5D)) than with EM3 (FIG. (5B)). EM2 and EM5 are colocalized exquisitely at this level (FIG. (5F)). As expected, the neocortical areas and the hippocampus showed a high density of diffuse and neuritic plaques, whereas the cortex of the cerebellum and the corpus striatum only displayed diffuse amyloid deposits. The sections incubated with the EM3 antibody displayed reactivity with diffuse and with neuritic plaques (FIG. (5B)). When they were compared with successive sections stained with the modified methenamine-silver method, it was shown that EM3 stained all the plaques present in each section. Additionally, the EM3 antibody stained some neuronal bodies. Both EM2 and EM5 stained immature neuritic plaques (without nucleus) and mature neuritic plaques (with nucleus), again with a high degree of colocalization (FIG. (5F)). EM2 did not react with any diffuse plaques, neither in the cortical region nor in the subcortical region (FIG. (3E)). Double immunostaining with EM5 and EM3 reveals the colocalization of both antibodies in some neuritic plaques, but not in diffuse plaques (FIG. (5C)), although some colocalization was found at this level when EM5 was incubated at a very low dilution (1:50). Only in one case, which displayed abundant EM3-positive diffuse plaques in sections of the corpus striatum, some of them were stained very slightly with EM5 at the working dilution (1:500). This same case did not show any reactivity of the diffuse plaques as EM5 in the cortex of the cerebellum. In all other cases the sections of the corpus striatum and of the cerebellum showed a variable amount of diffuse plaques, none of them reactive to the EM5 antibody. Neither EM2 nor EM5 appeared to stain all the neuritic plaques present (see FIG. (5A, D)). However, as had been observed in the case of the immunoreactivity of the vascular amyloid deposits, the neuritic plaques reactive to EM2 or EM5 were stained more intensely than with EM3. Apart from negativity of the vessels to all the antibodies in a single case and the slight positivity of some diffuse plaques of the corpus striatum in this same brain, it can be considered that all cases show similar patterns of staining for each antibody tested.

Thus, in contrast to the more uniform pattern of staining observed in the diffuse plaques, the panel of antibodies detected heterogeneity among the neuritic plaques, which proves relevant for indicating actual stages in the process of development of the diffuse plaques and their transformation to neuritic plaques. The EM5 antibody gave intense staining of all the structures (neuritic plaques and vessel walls) stained by EM2 and stained to a variable degree by EM3. A subset of neuritic plaques was found to have a pattern of staining identical to the vascular amyloid, with high colocalization of reactivity to EM2 and EM5. The invention shows that EM5 ought to react with all the structures that contain either $A\beta_{<11-40}$ or $A\beta_{<11-42}$. In fact, the ELISA results presented here show that the EM5 antibody recognizes both recently dissolved and aggregated forms of the Aβ peptide. However, in tissue sections we found greater variability of staining between the neuritic plaques with EM5 than with the polyclonal antibodies, together with high colocalization of intense reactivity to EM5 with EM2 (Aβ C40). Relatively more intense staining in these positive plaques may reveal a subgroup of neuritic plaques either with a particularly high content of long Aβ peptides, or selectively high content of Aβ C40, or even particular accessibility of the epitope recognized by EM5 in structures (vessels or plaques) that show codeposition of $A\beta_{<11-40}$ and $A\beta_{<11-42}$. The antibody of the invention seems to detect the same subset of neuritic plaques Aβ C40 (+) detected previously by Parvathy et al. [22]. This subset of neuritic plaques with particularly high contents of long Aβ peptides may represent important milestones in the progression of the amyloid lesions in AD that the monoclonal antibody of the invention is able to detect. Therefore, the use of EM5 can permit subsets of plaques to be defined that constitute a specific marker of the stage of progression of the disease.

Example 6

Capacity of the Antibodies for Reacting with Forms of β-Amyloid Peptide in Urine To demonstrate the validity of the EM5 antibody for detecting the presence of forms of β-amyloid peptide in biological fluids, a test was carried out for detecting them in urine samples from healthy patients, to which a mixture of synthetic peptides that corresponded to forms of different length of β-amyloid peptide had been added after they were obtained. For this, the monoclonal antibody, bound to magnetic particles, was added to the urine samples, and the bound peptides were detected using MALDI-TOF mass spectrometry. The details of the method employed are presented below.

Binding of the Antibody to Magnetic Particles

The magnetic particles coupled to the EM5 antibody were prepared following the method described by Fuentes et al. [26], based on gentle oxidation of the glycoside residues of the immunoglobulins to generate aldehyde groups, which are reacted with magnetic particles, on the surface of which amino groups have been generated by modification with ethylenediamine. Briefly, oxidation of the EM5 antibody was induced by incubation with sodium periodate 10 mM for 2 hours, after which the oxidized antibody was dialysed in distilled water at 4° C. EM/100-30 magnetic particles (Merck Co, France), which have carboxyl groups on their surface, were modified by incubation, at a concentration of 10 mg/ml, with 1M ethylenediamine pH 4.75, for 90 minutes, after which solid EDCl (1-ethyl-3-(3'-dimethylaminopropyl)carbodiimide hydrochloride) was added to a final concentration of 10 mM and was left to react for 90 minutes, before washing profusely with distilled water.

The antibody was immobilized on the magnetic particles after adding 10 mg of the oxidized EM5 antibody, dissolved in sodium phosphate buffer 150 mM of pH 7.5, to 2 ml of magnetic particles (10 mg/ml) with amino groups on their surface at 4° C. and incubating overnight. The Schiff bases formed and the unreacted aldehyde groups were reduced by adding sodium borohydride until a concentration of 1 mg/ml was reached, at pH 8.5 and 4° C. The preparation was washed with copious amounts of distilled water. The amount of antibody immobilized was determined by quantifying the difference in concentration of proteins in the supernatant before and after immobilization, using Bradford's method [27].

Detection of β-Amyloid Peptide in Solution

Before verifying its validity for binding to isoforms of β-amyloid peptide present in samples of biological fluids such as urine, we tested the capacity of the antibody of the invention for binding to forms of β-amyloid peptide in solution and whether the antibodies coupled to magnetic particles made it possible to extract forms of β-amyloid peptide from solutions in which they occurred, to proceed to their subsequent identification and/or quantification. Therefore, synthetic peptides that corresponded to the forms of β-amyloid peptide $A\beta_{12-29}$, $A\beta_{1-40}$ and $A\beta_{1-42}$, dissolved in distilled water, were mixed together in distilled water to give a mixture with final concentrations of 0.44 µg/µl of $A\beta_{12-29}$ and $A\beta_{1-42}$ and 0.11 µg/µl of $A\beta_{1-40}$. 4 µl of this mixture of peptides was added to 981 µl of water.

Next, the forms of β-amyloid peptide present in solution in water were separated using the antibody of the invention, coupled to magnetic particles. Mass spectrometry analysis of the mixtures of peptides separated from the solution is shown in FIG. 6, in which part A corresponds to analysis of the solution without prior treatment with antibodies (Ctrl.) and part B corresponds to the use of the antibody bound to magnetic particles (EM5+PM). As can be seen, the antibody is capable of binding to forms of β-amyloid peptide in solution and of forming complexes with them, so that they can be separated from said solution.

Preparation of the Urine Sample

On separate days, 10-ml samples of urine were collected from a healthy individual and were centrifuged at 3500 rpm at room temperature for 5 minutes. The urine was neutralized to pH 7.0 with 1 M NaOH in PBS buffer.

Synthetic peptides that corresponded to the forms of β-amyloid peptide $A\beta_{12-28}$, $A\beta_{1-40}$ and $A A\beta_{1-42}$, were mixed together in distilled water to give a mixture with final concentrations of 0.44 µg/µl of $A\beta_{12-28}$ and $A\beta_{1-42}$ and 0.11 µg/µl of $A\beta_{1-40}$. 4 µl of this mixture of peptides was added to 981 µl of urine.

The final concentration of forms of β-amyloid peptide in urine was 1.76 µg/ml in the case of $A\beta_{12-18}$ and of $A\beta_{1-42}$ and 0.44 µg/ml in the case of $A\beta_{1-40}$.

Immunoprecipitation

15 µl of magnetic particles coated with the EM5 monoclonal antibody (diluted 1:4 in PBS buffer) were incubated for 1 hour at 37° C. with 981 µl of the urine sample described above, which contained the three β-amyloid peptides ($A\beta_{12-18}$, $A\beta_{1-40}$ and $A\beta_{1-42}$).

After incubation, the tube was placed in a magnetized separator of magnetic particles and the urine was extracted carefully using a pipette.

The magnetic particles with the peptides bound to them, retained by the action of the magnetic field of the separator, were washed 3 times with $H_2O$.

The peptides bound to them were separated from the magnetic particles with 12 µl of a solution of a matrix of α-cyano-4-hydroxycinnamic acid in 30% (v/v) of aqueous acetonitrile containing 0.1% (v/v) of trifluoroacetic acid (TFA) and were analyzed by MALDI-TOF mass spectrometry.

Detection of the Immunoprecipitated Peptides by Mass Spectrometry 1.5 µl of the sample mixture resulting from immunoprecipitation in the matrix of α-cyano-4-hydroxycinnamic acid was placed in a stainless steel probe with capacity for 100 samples and left to dry at room temperature for 5 minutes.

The samples were measured in a workstation for MALDI-TOF mass spectrometry Voyager DE-PRO from PE Biosystems using the default configuration of the instrument. The mass spectra were recorded in positive reflector mode at an accelerating voltage of 20 kV and a collector voltage of 75%, 0.002% of guide filament and 150 nanoseconds of lag time, accumulating 200 spectra of individual laser firings below the threshold irradiation. Only mass signals with good resolution, of high intensity, from 3-5 selected points of incidence, were considered. The equipment was calibrated externally using calibration mixture 2, supplied by Applied Biosystems (Tres Cantos, Madrid, Spain), composed of angiotensin (1297 Da), ACTH 1-17 (2094 Da), ACTH 18-39 (2466 Da), ACTH 7-38 (3660 Da) and bovine insulin (2867 Da).

FIG. 7 shows the graph obtained with one of the samples, which is representative of the others. Peaks can be seen that correspond to the peptides added to the urine sample, which demonstrates the capacity of the antibody of the invention for binding to them in urine samples. As the analysis had been carried out with a sample of a biological fluid, other peaks can also be seen, corresponding to other molecules naturally present in the sample and which also became bound to the antibody coupled to magnetic particles.

Deposition of the Hybridoma

The hybridoma that produces the EM5 antibody was deposited in the European Collection of Cell Cultures (ECACC), CAMR, Salisbury, Wiltshire, United Kingdom. The date of deposition and the access number are as follows:

| Designation of the hybridoma | Date of deposition | Access No. |
|---|---|---|
| EM5 clone A | 03.01.2006 | 06030101 |

As noted previously, these hybridoma cells were obtained by fusion of two types of cells: a) BALB/c mouse spleen lymphocytes, obtained after immunization of the mice using, as immunogen, the form of β-amyloid peptide designated Aβ$_{1-40}$, comprising amino acids 1 to 40 of said peptide, coupled to KLH (keyhole limpet heamocyanin); b) cells of the mouse myeloma line P31×63-Ag653, which acted as the immortal part in the fusion. Various clones were obtained, from which we selected the clone designated "EM5 clone A", which produces the monoclonal antibody designated "EM5", a type IgG1 antibody capable of specifically recognizing the antigen used for immunization, the peptide Aβ$_{1-40}$, as verified by antibody capture tests of the ELISA type. This clone was grown in RPMl 1640 culture medium with 10% fetal calf serum, 10% DMSO, glutamine 2 mM and sodium pyruvate 1 mM, at 37° C. and in an atmosphere with 5% $CO_2$, conditions in which 95% of the cells grew in suspension and the remaining 5% adhered to the culture vessel, The cells were cloned twice by means of limiting dilutions, after which aliquots of $4×10^6$ cells were taken, and were placed in vials. After controlling for absence of bacteria, absence of mycoplasmas and absence of fungi, several of these vials were sent to the European Collection of Cell Cultures (ECACC), requesting permission for their deposition.

REFERENCES

1. Dickson D W, Crystal H A, Mattiace L A, Masur D M, Blau A D, Davies P, Yen S. and Aronson M K. Identification of normal and pathological aging in prospectively studied nondemented elderly humans. Neurobiol Aging 13: 1-11 (1992).
2. Iwatsubo T, Mann D A M, Odaka A, Suzuki N and Ihara Y. Amyloid β protein (Aβ) deposition: Aβ42(43) precedes Aβ40 in Down's syndrome. Ann Neurol 37: 294-299 (1995).
3. Fukumoto H, Asami-Okada A, Suzuki N, Shimada H, Ihara Y and Iwatsubo T. Amyloid β protein deposition in normal aging has the same characteristics as that in Alzheimer's disease. Am J Pathol 148: 259-265 (1996).
4. Giaccone G, Tagliavini F, Linoli G, Bouras C, Frigerior L, Frangione B and Bugiani O. Down syndrome patients: extracellular preamyloid deposits precede neuritic degeneration and senile plaques. Neurosci Lett 97: 232-238 (1989).
5. Terry R D, Masliah E, Salmon D P, Butters N, DeTeresa R, Hill R, Hansen L A, Katzman R. Physical basis of cognitive alterations in Alzheimer's disease: synapse loss is the major correlate of cognitive impairment. Ann Neurol 30: 572-580 (1991).
6. Masliah E, Terry R D, Mallory M, Alford M and Hansen L A. Diffuse plaques do not accentuate synapse loss in Alzheimer Disease. Am J Path 137: 1293-97 (1990).
7. Dickson D W. The pathogenesis of senile plaques. J Neuropathol Exp Neurol 56: 321-339 (1997).
8. Braak H and Braak E. Neuropathological staging of Alzheimer-related changes. Acta Neuropathologica (Berl) 82: 239-259 (1991).
9. Thal D R, Rüb U, Schultz Ch, Sassin I, Ghebremedhin S, Del Tredici K, Braak E and Braak H. Sequence of Aβ-protein deposition in the human medial temporal lobe, J Neuropathol Exp Neurol 59 (8): 733-748 (2000).
10. Mirra, S S, Heyman A, McKeel D, Sumi S M, Crain B J, Brownlee L M, Vogel F S, Hughes J P, van Belle G and Berg L. The Consortium to Establish a Registry for Alzheimer's Disease (CERAD). Part II. Standardization of the neuropathologic assessment of Alzheimer's disease. Neurology, 41: 479-486 (1991).
11. Selkoe D J. Alzheimer's disease: genotypes, phenotype and treatments. Science 275(5300):630-1 (1997).
12. Hardy J, and Selkoe D J. The amyloid hypothesis of Alzheimer's disease: progress and problems on the road to therapeutics. Science 297: 353-356 (2002).
13. Vigo-Pelfrey C, Lee D, Keim P, Lieberberg I and Schenk D B. Characterization of β-amyloid peptide from human cerebrospinal fluid. J. Neurochem 61: 1965-1968 (1993).
14. Iwatsubo T, Mann D A M, Odaka A, Suzuki N and Ihara Y. Amyloid β protein (Aβ) deposition: Aβ42(43) precedes Aβ40 in Down's syndrome. Ann. Neurol 37: 294-299 (1995)
15. Iwatsubo T, Saido T C, Mann D M A, Lee V M-Y and Trojanowski J Q. Full-length amyloid-β (1-42(43)) and amino-terminally modified and truncated amyloid-β42 (43) deposit in diffuse plaques. Am J Pathol 149: 1823-1830 (1996).
16. Higgins L, Murphy Jr G M, Fomo L S, Catalano R and Cordell B. P3 β-amyloid peptide has a unique and potentially pathogenic immunohistochemical profile in Alzheimer's disease brain. Am J Path 149: 585-596 (1996).
17. Gowing E, Roher A E, Woods A S, Cotter R J, Chaney M, Little S P and Ball M J. Chemical characterization of Aβ 17-42 peptide, a component of diffuse amyloid deposits of Alzheimer disease. J Biol Chem 269: 10987-10990 (1994).
18. Kida E, Wisniewski K E and Wisniewski H M. Early amyloid-β deposits show different immunoreactivity to the amino- and carboxy-terminal regions of β-peptide in Alzheimer's disease and Down's syndrome brain. Neurosci Lett 193: 105-108 (1995).
19. Lalowski M, Golabek A, Lemere A, Selkoe D J, Wisniewski H M, Beavis R C, Frangione B and Wisniewski T. The "nonamyloidogenic" p3-fragment (amyloid β17-42) is a major constituent of Down's syndrome cerebellar preamyloid. J Biol Chem 271: 33623-33631 (1994).
20, Saido T C, Iwatsubo T, Mann D M A, Shimada H, Ihara Y and Kawashima S. Dominant and differential deposition of distinct β-amyloid peptide species, AβN3(peptide) in senile plaques. Neuron, 14:457-466 (1995).
21. Tekirian T L, Saido T C, Markesberry W R, Russell M I, Wekstein D R, Patel E and Geddes J W. N-terminal heterogeneity of parenchymal and cerebrovascular Aβ deposits. J Neuropathol Exp Neurol 57: 76-94 (1998).
22. Parvathy S, Davis P, Haroutunian V, Purohit D P, Davis K L, Mohs R C, Park H, Moran T M, Chan J Y and Buxbaum J D. Correlation between Aβ$_{1-40}$, Aβ$_{1-42}$, and Aβ$_{1-43}$-containing amyloid plaques and cognitive decline. Arch Neurol 58: 2025-2032 (2001).
23. Larner A J. Hypothesis: amyloid β peptides truncated at the N-terminus contribute to the pathogenesis of Alzheimer's disease. Neurobiol Aging 20: 65-69 (1999).
24. Jimenez-Huete A, Alfonso P, Soto C, Alvar J P, Rabano A, Ghiso B, Frangione B and Mendez E. Antibodies directed to the carboxyl terminus of amyloid O-peptide recognize sequence epitopes and distinct immunoreactive deposits in Alzheimer's disease brain Alzheimer's Reports 1: 4148 (1998).
25. Campbell A. Monoclonal antibody technology In: "Laboratory Techniques in Biochemistry and Molecular Biology" Eds: Burdon R H, Knippenberg P R) Elsevier, Amsterdam, p. 120-134 (1984).
26. Fuentes M, Mateo C, Guisan J M, Fernandez-Lafuente R. Preparation of inert magnetic nano-particles for the directed immobilization of antibodies. Biosensors and Bioelectronics 20: 1380-1387. (2005)
27. Bradford M M. A rapid and sensitive method for the quantification of microgram quantities of protein using the principle of protein-β binding. Anal. Biochem. 72: 278-254. (1976)
28. Mayeux R, Ong L S, Tang M-X, Manly J, Stem Y, Schupf N, Mehta P D. Plasma Aβ40 and Aβ42 and Alzheimer disease. Relation to age, mortality and risk. Neurology 61: 1185-1190. (2003).
29. Vandersthichele H, van Kerscliaver E, Hesse C, Davidsson P, Buyse M, Andreasen N, Minthon L, Tallin A, Blennow K, Vanmechelen E. Standardization of measurement of beta-amyloid (1-42) in cerebrospinal fluid and plasma Amyloid 7: 245-258. (2000).
30. Ghiso J, Calero M, Matsubara E, Governale S, Chuba J, Beavis R, Wisniewski T, Frangione B. Alzheimer's soluble amyloid beta is a normal component of human urine. FEBS Lett 408: 105-108 (1997).

The invention claimed is:

1. A monoclonal antibody that recognizes, in β-amyloid peptide (AP), an epitope consisting of the sequence:
Val-His-His-Gln-Lys (SEQ ID NO:3)
wherein the antibody binds to isoforms of human β-amyloid peptide that contain said sequence, both in aggregate form and in solution, without binding to isoforms of human β-amyloid protein that do not contain the sequence, and wherein the antibody has a binding affinity to $A\beta_{1-42}$ that is greater than its binding affinity to $A\beta_{1-40}$ as measured by ELISA.

2. The monoclonal antibody as claimed in claim 1, which is produced by the hybridoma cell line ECACC 06030101.

3. A hybridoma cell line capable of producing the monoclonal antibody as claimed in claim 1.

4. The hybridoma cell line as claimed in claim 3, obtained by fusion with the mouse myeloma line P3/X63-Ag.653 of spleen cells of BALB/c mice immunized with at least one peptide that contains the sequence Val-His-His-Gln-Lys (SEQ ID NO: 3).

5. The hybridoma cell line as claimed in claim 3, obtained by fusion with the mouse myeloma line P3/X63-Ag.653 of spleen cells of BALB/c mice immunized with the peptide $A\beta_{1-40}$.

6. The hybridoma cell line as claimed in claim 5, obtained by fusion with the mouse myeloma line P3/X63-Ag.653 of spleen cells of BALB/c mice immunized with the peptide $A\beta_{1-40}$ coupled to KLH.

7. The hybridoma cell line as claimed in claim 6, which comprises a substantially pure sample of ECACC 06030101.

8. A composition that comprises the monoclonal antibody of claim 1 or an antigen binding fragment thereof, coupled to a substance that permits said antibody or a fragment thereof to be detected.

9. The composition as claimed in claim 8, wherein the substance to which the monoclonal antibody is coupled is a second antibody capable of binding to said first antibody, this second antibody being bound to an enzyme capable of catalyzing the conversion of a particular substance to another that can be detected.

10. The composition as claimed in claim 9, wherein the substance whose conversion is catalyzed by the enzyme is a chromogen.

11. The composition as claimed in claim 10, wherein the second antibody is bound to alkaline phosphatase and the chromogen used is nitroblue tetrazolium.

12. The composition as claimed in claim 10, wherein the second antibody is bound to radish peroxidase and the chromogen used is diaminobenzidine.

13. The composition as claimed in claim 8, further comprising one or more antibodies that bind to β-amyloid peptide at sequence regions other than SEQ ID NO:3.

14. The composition as claimed in claim 13, wherein the monoclonal antibody or antigen-binding fragment thereof is coupled to one substance that can be detected, and the one or more antibodies that bind to β-amyloid peptide sequence regions other than SEQ ID NO:3 are coupled to different substances that can be detected.

15. The composition as claimed in claim 14, wherein the one or more antibodies that bind to β-amyloid peptide sequence regions other than SEQ ID NO: 3 comprise a polyclonal antibody that recognizes an epitope at the carboxyl terminus of amyloid β-peptide.

16. The composition as claimed in claim 15, wherein the monoclonal antibody is coupled to a second antibody bound to radish peroxidase, and the polyclonal antibody is coupled to a second antibody bound to alkaline phosphatase.

17. A composition that comprises a monoclonal antibody as claimed in claim 2, wherein the antibody is coupled to a substance or particle that facilitates the extraction of antigen-antibody fragment complexes from the solution in which they occur.

18. The composition as claimed in claim 17, wherein the substance or particle that facilitates the extraction of antigen-antibody complexes from the solution in which they occur is a magnetic particle.

19. The composition as claimed in claim 18, wherein the bond between the antibody and the magnetic particle is a covalent bond.

20. A method of in-vitro diagnosis of Alzheimer's disease from a biological sample taken from an individual, comprising the steps of:
(a) providing the monoclonal antibody of claim 1 or an antigen-binding fragment thereof;
(b) contacting the sample with the monoclonal antibody; and
(c) detecting whether the monoclonal antibody binds material in the sample to determine whether neuritic plaques and/or the vascular amyloid deposits are present in the sample.

21. The method as claimed in claim 20, wherein the monoclonal antibody is contained in a composition and is coupled to a substance that permits the antibody or fragment thereof to be detected.

22. The method as claimed in claim 20, further comprising quantifying the number of neuritic plaques detected in part (c) and correlating the number with a stage of progression of the disease.

23. The method claimed in claim 20, wherein the presence of $A\beta_{1-40}$ of β-amyloid in the sample is confirmed through the binding of an antibody specific for the carboxyterminal of the $A\beta_{1-40}$ isoform of the β-amyloid peptide.

24. The method as claimed in claim 20, wherein the presence of additional neuritic plaques and/or diffuse plaques is detected through the binding of an antibody specific for the carboxy-terminal of the $A\beta_{1-42}$ isoform of the β-amyloid peptide.

25. The method as claimed in claim 20, wherein the sample comprises a biological fluid or solution derived therefrom.

26. The method as claimed in claim 25, wherein the sample comprises cerebrospinal fluid, blood, plasma or urine.

27. The method as claimed in claim 26, wherein the sample comprises urine.

28. The method as claimed in claim 25, wherein the monoclonal antibody is contained in a composition wherein the antibody is coupled to a substance or particle that facilitates the extraction of antigen-antibody fragment complexes from the solution in which they occur.

29. The method as claimed in claim 28, wherein the substance or particle is a magnetic particle and wherein the bond between the antibody and the magnetic particle is a covalent bond.

30. The method as claimed in claim 29, wherein the composition is added to the sample of biological fluid or to the solution derived therefrom in order to form antigen-antibody complexes with the forms of the β-amyloid peptide present in the sample of biological fluid or the solution derived therefrom.

31. The method as claimed in claim 30, further comprising bringing the sample comprising antigen-antibody complexes into contact with a magnetic field.

32. The method as claimed in claim 31, further comprising the steps of separating antigen from the antigen-antibody complexes and identifying and/or quantifying the forms of β-amyloid peptide.

33. The method as claimed in claim 32, wherein the forms of β-amyloid peptide are identified and/or quantified by means of MALDI-TOF mass spectrometry.

34. The method as claimed in claim 28, wherein the sample of biological fluid is a sample of urine.

35. The method as claimed in claim 28, wherein the stage of progression of Alzheimer's disease is correlated to the concentration of the $A\beta_{1-42}$ isoform in the sample.

36. The method according to claim 20, wherein the sample comprises brain tissue taken from an individual suspected of having Alzheimer's disease.

37. A method of in-vitro diagnosis of Alzheimer's disease from a sample of a biological fluid or of a solution derived therefrom that comprises the detection, from said sample, of at least one isoform of β-amyloid peptide that contains at least the sequence Val-His-His-Gln-Lys (SEQ ID NO:3) through its binding to a monoclonal antibody that comprises the stages of:
 a) addition of a composition as claimed in claim 18 to the sample of biological fluid or the solution derived therefrom;
 b) waiting a sufficient time for antigen-antibody complexes to form between at least one isoform of β-amyloid peptide and the antibody contained in the composition;
 c) application of a magnetic field for extracting the antigen-antibody complexes from the solution;
 d) removal of the solution;
 e) separation of the antibody from the molecules of β-amyloid peptide;
 f) identification and quantification of the isoforms of β-amyloid peptide extracted from the sample of biological fluid or solution derived therefrom.

38. The method of in-vitro diagnosis of Alzheimer's disease as claimed in claim 37, wherein the sample of biological fluid is a sample of urine.

39. The method of in-vitro diagnosis of Alzheimer's disease as claimed in claim 38, wherein the composition that is added in stage a) comprises the monoclonal antibody bound covalently to the corresponding magnetic particles by modification of one or more residues present in the Fc region of said antibody.

40. The method of in-vitro diagnosis of Alzheimer's disease as claimed in claim 39, wherein the identification and quantification of the isoforms of β-amyloid peptide extracted from the sample of urine are carried out by MALDI-TOF mass spectrometry.

41. The method of in-vitro diagnosis of Alzheimer's disease as claimed in claim 40, wherein stage e) of separation of the antibody from the molecules of β-amyloid peptide is carried out in α-cyano-4-hydroxycinnamic acid in aqueous'acetonitrile containing trifluoroacetic acid.

* * * * *